(12) United States Patent
Hinderer et al.

(10) Patent No.: US 8,207,112 B2
(45) Date of Patent: Jun. 26, 2012

(54) LIQUID FORMULATION OF G-CSF CONJUGATE

(75) Inventors: Walter Hinderer, Rodgau (DE); Christian Scheckermann, Merzhausen (DE)

(73) Assignee: BioGeneriX AG, Ulm (DE)

( * ) Notice: Subject to any disclaimer, the term of this patent is extended or adjusted under 35 U.S.C. 154(b) by 0 days.

(21) Appl. No.: 12/201,705

(22) Filed: Aug. 29, 2008

(65) Prior Publication Data

US 2009/0143292 A1 Jun. 4, 2009

Related U.S. Application Data

(60) Provisional application No. 60/968,735, filed on Aug. 29, 2007.

(51) Int. Cl.
| A61K 38/18 | (2006.01) |
| A61K 38/00 | (2006.01) |
| C07K 14/475 | (2006.01) |
| A61P 7/00 | (2006.01) |
| A61P 7/06 | (2006.01) |

(52) U.S. Cl. .......................... 514/7.6; 514/7.9; 514/8.3
(58) Field of Classification Search .................. None
See application file for complete search history.

(56) References Cited

U.S. PATENT DOCUMENTS

| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts et al. |
| 4,412,989 A | 11/1983 | Iwashita et al. |
| 4,414,147 A | 11/1983 | Klibanov |
| 4,438,253 A | 3/1984 | Casey et al. |
| 4,496,689 A | 1/1985 | Mitra |
| 4,565,653 A | 1/1986 | Ives et al. |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,925,796 A | 5/1990 | Bergh et al. |
| 5,032,519 A | 7/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,169,933 A | 12/1992 | Anderson et al. |
| 5,182,107 A | 1/1993 | Friden |
| 5,194,376 A | 3/1993 | Kang |
| 5,202,413 A | 4/1993 | Spinu |
| 5,219,564 A | 6/1993 | Zalipsky et al. |
| 5,281,698 A | 1/1994 | Nitecki |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot |
| 5,369,017 A | 11/1994 | Wong et al. |
| 5,374,541 A | 12/1994 | Wong |
| 5,374,655 A | 12/1994 | Kashem et al. |
| 5,405,753 A | 4/1995 | Brossmer |
| 5,410,016 A | 4/1995 | Hubbell et al. |
| 5,432,059 A | 7/1995 | Bean |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,583,042 A | 12/1996 | Roth |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,716,812 A | 2/1998 | Withers et al. |
| 5,723,121 A | 3/1998 | Takenaga et al. |
| 5,728,554 A | 3/1998 | Bayer et al. |
| 5,770,420 A | 6/1998 | Lowe et al. |

(Continued)

FOREIGN PATENT DOCUMENTS

DE 19852729 A1 5/2000

(Continued)

OTHER PUBLICATIONS

Abuchowski et al., *J. Biol. Chem.*, 252(11): 3582-3586 (1977).
Amersham Pharmacia Biotech, "Hydrophobic Interaction Chromatography: Principles and Methods," 104 pp. (2000).
Barrios et al., *J. Mol. Recognit.*, 17(4):332-338 (2004).
Bijsterbosch et al., *Eur. J. Biochem.*, 237(2): 344-349 (1996).

(Continued)

*Primary Examiner* — Robert Landsman
(74) *Attorney, Agent, or Firm* — Leydig, Voit & Mayer, Ltd.

(57) ABSTRACT

The present invention relates to a liquid pharmaceutical composition comprising a granulocyte colony stimulating factor polypeptide conjugated with a polymer. In various embodiments, the composition has a pH value in the range of 4.5 to 5.5. Exemplary compositions further comprise a surfactant and optionally one or more other pharmaceutically acceptable excipients. The invention provides, inter alia, formulations free from tartaric acid or salts thereof and/or from succinic acid and salts thereof as buffering agents. Exemplary formulations are essentially devoid of not amino acids as stabilizers. The composition has good storage stability and is especially useful for the prophylaxis and treatment of disorders and medical indications where granulocyte colony stimulating factor preparations are considered as useful remedies.

37 Claims, No Drawings

U.S. PATENT DOCUMENTS

| | | | |
|---|---|---|---|
| 5,798,233 | A | 8/1998 | Gotschlich |
| 5,811,238 | A | 9/1998 | Stemmer et al. |
| 5,824,778 | A | 10/1998 | Ishikawa et al. |
| 5,824,864 | A | 10/1998 | Fox et al. |
| 5,830,721 | A | 11/1998 | Stemmer et al. |
| 5,833,988 | A | 11/1998 | Friden |
| 5,834,251 | A | 11/1998 | Maras et al. |
| 5,837,458 | A | 11/1998 | Minshull et al. |
| 5,849,535 | A | 12/1998 | Cunningham et al. |
| 5,858,751 | A | 1/1999 | Paulson et al. |
| 5,858,752 | A | 1/1999 | Seed et al. |
| 5,874,075 | A * | 2/1999 | Collins et al. ............... 424/85.1 |
| 5,876,980 | A | 3/1999 | DeFrees et al. |
| 5,922,577 | A | 7/1999 | DeFrees et al. |
| 5,932,462 | A | 8/1999 | Harris et al. |
| 5,945,314 | A | 8/1999 | Prieto et al. |
| 5,945,322 | A | 8/1999 | Gotschlich |
| 5,955,347 | A | 9/1999 | Lowe |
| 5,962,294 | A | 10/1999 | Paulson et al. |
| 5,969,040 | A | 10/1999 | Hallahan et al. |
| 5,977,307 | A | 11/1999 | Friden |
| 6,010,999 | A | 1/2000 | Daley et al. |
| 6,015,555 | A | 1/2000 | Friden |
| 6,030,815 | A | 2/2000 | DeFrees et al. |
| 6,034,223 | A | 3/2000 | Maddon et al. |
| 6,037,452 | A | 3/2000 | Minamino et al. |
| 6,057,292 | A | 5/2000 | Cunningham et al. |
| 6,075,134 | A | 6/2000 | Bertozzi et al. |
| 6,087,325 | A | 7/2000 | Meers et al. |
| 6,096,512 | A | 8/2000 | Elhammer et al. |
| 6,113,906 | A | 9/2000 | Greenwald et al. |
| 6,117,651 | A | 9/2000 | Schultz et al. |
| 6,166,183 | A | 12/2000 | Ishikawa et al. |
| 6,183,738 | B1 | 2/2001 | Clark |
| 6,261,805 | B1 | 7/2001 | Wood |
| 6,268,193 | B1 | 7/2001 | Lowe |
| 6,319,695 | B1 | 11/2001 | Wong et al. |
| 6,342,382 | B1 | 1/2002 | Gotschlich |
| 6,348,558 | B1 | 2/2002 | Harris et al. |
| 6,362,254 | B2 | 3/2002 | Harris et al. |
| 6,376,604 | B2 | 4/2002 | Kozlowski |
| 6,399,336 | B1 | 6/2002 | Paulson et al. |
| 6,399,337 | B1 | 6/2002 | Taylor et al. |
| 6,440,703 | B1 | 8/2002 | DeFrees |
| 6,465,220 | B1 | 10/2002 | Hassan et al. |
| 6,531,121 | B2 | 3/2003 | Brines et al. |
| 6,555,346 | B1 | 4/2003 | Kretzdorn et al. |
| 6,555,660 | B2 * | 4/2003 | Nissen et al. ............... 530/397 |
| 6,586,398 | B1 | 7/2003 | Kinstler et al. |
| 6,692,931 | B1 | 2/2004 | Reutter et al. |
| 6,693,183 | B2 | 2/2004 | Natsuka et al. |
| 6,716,626 | B1 | 4/2004 | Itoh et al. |
| 6,743,896 | B2 | 6/2004 | Filpula et al. |
| 6,780,624 | B2 | 8/2004 | Gotschlich |
| 6,800,740 | B1 | 10/2004 | Cunningham et al. |
| 6,949,372 | B2 | 9/2005 | Betenbaugh et al. |
| 7,094,530 | B1 | 8/2006 | Sasaki et al. |
| 7,125,843 | B2 | 10/2006 | DeFrees et al. |
| 7,138,371 | B2 | 11/2006 | DeFrees et al. |
| 7,157,277 | B2 | 1/2007 | DeFrees et al. |
| 7,173,003 | B2 | 2/2007 | DeFrees et al. |
| 7,179,617 | B2 | 2/2007 | DeFrees et al. |
| 7,202,208 | B2 | 4/2007 | Papadimitriou |
| 7,214,660 | B2 | 5/2007 | DeFrees et al. |
| 7,226,903 | B2 | 6/2007 | DeFrees et al. |
| 7,229,962 | B2 | 6/2007 | Chung et al. |
| 7,235,638 | B2 | 6/2007 | Persson |
| 7,265,084 | B2 | 9/2007 | DeFrees et al. |
| 7,265,085 | B2 | 9/2007 | DeFrees et al. |
| 7,276,475 | B2 | 10/2007 | DeFrees et al. |
| 7,297,511 | B2 | 11/2007 | DeFrees et al. |
| 7,304,150 | B1 | 12/2007 | Egrie et al. |
| 7,338,933 | B2 | 3/2008 | DeFrees et al. |
| 7,368,108 | B2 | 5/2008 | DeFrees et al. |
| 7,399,613 | B2 | 7/2008 | DeFrees et al. |
| 7,405,198 | B2 | 7/2008 | DeFrees et al. |
| 7,416,858 | B2 | 8/2008 | DeFrees et al. |
| 7,439,043 | B2 | 10/2008 | DeFrees et al. |
| 7,473,680 | B2 | 1/2009 | DeFrees et al. |
| 7,524,813 | B2 | 4/2009 | Zundel et al. |
| 7,662,933 | B2 * | 2/2010 | Kinstler et al. ............... 530/402 |
| 7,691,603 | B2 | 4/2010 | DeFrees |
| 7,696,163 | B2 | 4/2010 | DeFrees et al. |
| 7,795,210 | B2 | 9/2010 | DeFrees et al. |
| 7,803,777 | B2 | 9/2010 | DeFrees |
| 7,842,661 | B2 | 11/2010 | DeFrees et al. |
| 7,932,364 | B2 | 4/2011 | DeFrees et al. |
| 7,956,032 | B2 | 6/2011 | DeFrees et al. |
| 8,063,015 | B2 | 11/2011 | DeFrees et al. |
| 2002/0016003 | A1 | 2/2002 | Saxon et al. |
| 2002/0019342 | A1 | 2/2002 | Bayer |
| 2002/0037841 | A1 | 3/2002 | Papadimitriou |
| 2002/0115833 | A1 | 8/2002 | Burg et al. |
| 2002/0137134 | A1 | 9/2002 | Gerngross et al. |
| 2002/0142370 | A1 | 10/2002 | Paulson et al. |
| 2002/0150981 | A1 | 10/2002 | Canfield |
| 2002/0168323 | A1 | 11/2002 | Gonda et al. |
| 2002/0182586 | A1 | 12/2002 | Morris et al. |
| 2003/0027257 | A1 | 2/2003 | Iatrou et al. |
| 2003/0040037 | A1 | 2/2003 | Bayer |
| 2003/0083251 | A1 | 5/2003 | Westenfelder |
| 2003/0124645 | A1 | 7/2003 | Paulson et al. |
| 2003/0166212 | A1 | 9/2003 | Taylor et al. |
| 2003/0166525 | A1 | 9/2003 | Hoffmann et al. |
| 2003/0180835 | A1 | 9/2003 | Bayer |
| 2003/0186850 | A1 | 10/2003 | Clausen et al. |
| 2003/0195338 | A1 | 10/2003 | Chung et al. |
| 2003/0207406 | A1 | 11/2003 | Johnson et al. |
| 2004/0043446 | A1 | 3/2004 | DeFrees et al. |
| 2004/0063911 | A1 | 4/2004 | DeFrees et al. |
| 2004/0077836 | A1 | 4/2004 | DeFrees et al. |
| 2004/0082026 | A1 | 4/2004 | DeFrees et al. |
| 2004/0102607 | A1 | 5/2004 | Danishefsky et al. |
| 2004/0115168 | A1 | 6/2004 | DeFrees et al. |
| 2004/0126838 | A1 | 7/2004 | DeFrees et al. |
| 2004/0132640 | A1 | 7/2004 | DeFrees et al. |
| 2004/0136955 | A1 | 7/2004 | Barker |
| 2004/0137557 | A1 | 7/2004 | DeFrees et al. |
| 2004/0197875 | A1 | 10/2004 | Hauser et al. |
| 2005/0026266 | A1 | 2/2005 | Clausen et al. |
| 2005/0031584 | A1 | 2/2005 | DeFrees et al. |
| 2005/0064540 | A1 | 3/2005 | DeFrees et al. |
| 2005/0100982 | A1 | 5/2005 | DeFrees et al. |
| 2005/0106658 | A1 | 5/2005 | DeFrees et al. |
| 2005/0118672 | A1 | 6/2005 | DeFrees et al. |
| 2005/0143292 | A1 | 6/2005 | DeFrees et al. |
| 2005/0250678 | A1 | 11/2005 | DeFrees et al. |
| 2005/0269265 | A1 | 12/2005 | DeFrees |
| 2005/0271690 | A1 | 12/2005 | Gotschlich |
| 2005/0288490 | A1 | 12/2005 | Nakamoto et al. |
| 2006/0024286 | A1 | 2/2006 | Glidden |
| 2006/0030521 | A1 | 2/2006 | DeFrees et al. |
| 2006/0035224 | A1 | 2/2006 | Johansen |
| 2006/0111279 | A1 | 5/2006 | DeFrees et al. |
| 2006/0177892 | A1 | 8/2006 | DeFrees |
| 2006/0182714 | A1 | 8/2006 | Behrens et al. |
| 2006/0246544 | A1 | 11/2006 | Kang et al. |
| 2006/0276618 | A1 | 12/2006 | DeFrees et al. |
| 2006/0287223 | A1 | 12/2006 | DeFrees et al. |
| 2006/0287224 | A1 | 12/2006 | DeFrees et al. |
| 2007/0014759 | A1 | 1/2007 | DeFrees et al. |
| 2007/0026485 | A1 | 2/2007 | DeFrees et al. |
| 2007/0027068 | A1 | 2/2007 | DeFrees et al. |
| 2007/0032405 | A1 | 2/2007 | DeFrees et al. |
| 2007/0037966 | A1 | 2/2007 | Rasmussen et al. |
| 2007/0059275 | A1 | 3/2007 | DeFrees et al. |
| 2007/0105755 | A1 | 5/2007 | DeFrees et al. |
| 2007/0111926 | A1 | 5/2007 | Zundel et al. |
| 2007/0154992 | A1 | 7/2007 | DeFrees |
| 2007/0254834 | A1 | 11/2007 | DeFrees et al. |
| 2007/0254836 | A1 | 11/2007 | DeFrees et al. |
| 2008/0015142 | A1 | 1/2008 | DeFrees et al. |
| 2008/0050772 | A1 | 2/2008 | DeFrees et al. |
| 2008/0070275 | A1 | 3/2008 | DeFrees et al. |
| 2008/0102083 | A1 | 5/2008 | DeFrees et al. |
| 2008/0108557 | A1 | 5/2008 | Behrens et al. |
| 2008/0146494 | A1 | 6/2008 | DeFrees et al. |

| | | | |
|---|---|---|---|
| 2008/0146782 A1 | 6/2008 | DeFrees et al. | |
| 2008/0176790 A1 | 7/2008 | DeFrees | |
| 2008/0187955 A1 | 8/2008 | DeFrees et al. | |
| 2008/0200651 A1 | 8/2008 | Ostergaard et al. | |
| 2008/0206808 A1 | 8/2008 | DeFrees et al. | |
| 2008/0206810 A1 | 8/2008 | Johnson et al. | |
| 2008/0207487 A1 | 8/2008 | DeFrees et al. | |
| 2008/0242607 A1 | 10/2008 | DeFrees | |
| 2008/0242846 A1 | 10/2008 | DeFrees et al. | |
| 2008/0248959 A1 | 10/2008 | DeFrees | |
| 2008/0253992 A1 | 10/2008 | DeFrees et al. | |
| 2008/0255026 A1 | 10/2008 | DeFrees et al. | |
| 2008/0255040 A1 | 10/2008 | DeFrees | |
| 2008/0274958 A1 | 11/2008 | DeFrees | |
| 2008/0280818 A1 | 11/2008 | DeFrees | |
| 2008/0300173 A1 | 12/2008 | DeFrees | |
| 2008/0300175 A1 | 12/2008 | DeFrees et al. | |
| 2008/0305518 A1 | 12/2008 | Klausen et al. | |
| 2008/0305991 A1 | 12/2008 | DeFrees et al. | |
| 2008/0305992 A1 | 12/2008 | DeFrees et al. | |
| 2008/0318850 A1 | 12/2008 | DeFrees et al. | |
| 2008/0319183 A1 | 12/2008 | DeFrees et al. | |
| 2009/0028822 A1 | 1/2009 | DeFrees et al. | |
| 2009/0048440 A1 | 2/2009 | Felo et al. | |
| 2009/0053167 A1 | 2/2009 | DeFrees | |
| 2009/0054623 A1 | 2/2009 | DeFrees | |
| 2009/0055942 A1 | 2/2009 | Ostergaard et al. | |
| 2009/0081188 A1 | 3/2009 | DeFrees et al. | |
| 2009/0093399 A1 | 4/2009 | DeFrees et al. | |
| 2009/0124544 A1 | 5/2009 | DeFrees | |
| 2009/0137763 A1 | 5/2009 | DeFrees et al. | |
| 2009/0143292 A1 | 6/2009 | Hinderer et al. | |
| 2009/0169509 A1 | 7/2009 | DeFrees et al. | |
| 2009/0176967 A1 | 7/2009 | Stennicke | |
| 2009/0203579 A1 | 8/2009 | DeFrees et al. | |
| 2009/0227504 A1 | 9/2009 | Klausen et al. | |
| 2009/0240028 A1 | 9/2009 | Behrens et al. | |
| 2009/0247450 A1 * | 10/2009 | Mack ................................ 514/8 | |
| 2009/0252720 A1 | 10/2009 | Ostergaard et al. | |
| 2009/0253166 A1 | 10/2009 | Zundel et al. | |
| 2009/0264366 A1 | 10/2009 | Johansen et al. | |
| 2009/0292110 A1 | 11/2009 | DeFrees | |
| 2009/0305967 A1 | 12/2009 | DeFrees et al. | |
| 2010/0009902 A1 | 1/2010 | DeFrees | |
| 2010/0015684 A1 | 1/2010 | DeFrees et al. | |
| 2010/0028939 A1 | 2/2010 | Behrens et al. | |
| 2010/0029555 A1 * | 2/2010 | Tonon et al. ..................... 514/12 | |
| 2010/0035299 A1 | 2/2010 | DeFrees et al. | |
| 2010/0041872 A1 | 2/2010 | DeFrees et al. | |
| 2010/0048456 A1 | 2/2010 | DeFrees et al. | |
| 2010/0056428 A1 | 3/2010 | Behrens | |
| 2010/0075375 A1 | 3/2010 | DeFrees et al. | |
| 2010/0081791 A1 | 4/2010 | DeFrees et al. | |
| 2010/0113743 A1 | 5/2010 | DeFrees et al. | |
| 2010/0120666 A1 | 5/2010 | Zopf et al. | |
| 2010/0174059 A1 | 7/2010 | DeFrees et al. | |
| 2010/0210507 A9 | 8/2010 | DeFrees et al. | |
| 2010/0286067 A1 | 11/2010 | DeFrees | |
| 2010/0322940 A1 | 12/2010 | Bayer | |
| 2010/0330645 A1 | 12/2010 | DeFrees et al. | |
| 2010/0331489 A1 | 12/2010 | DeFrees | |
| 2011/0003744 A1 | 1/2011 | DeFrees et al. | |
| 2011/0177029 A1 | 7/2011 | DeFrees | |
| 2011/0223646 A1 | 9/2011 | Schwartz et al. | |
| 2011/0318780 A1 | 12/2011 | DeFrees | |
| 2012/0016105 A1 | 1/2012 | DeFrees et al. | |

FOREIGN PATENT DOCUMENTS

| | | |
|---|---|---|
| EP | 0370205 A2 | 5/1990 |
| EP | 0474313 A | 3/1992 |
| EP | 0585109 A | 3/1994 |
| EP | 0605963 A2 | 7/1994 |
| EP | 1428878 A1 | 6/2004 |
| JP | H03-503759 A | 8/1991 |
| JP | H10-307356 A | 11/1998 |
| JP | H10-540638 A | 10/2001 |
| WO | WO 87/00056 | 1/1987 |
| WO | WO 87/05330 A1 | 9/1987 |
| WO | WO 89/06546 A1 | 7/1989 |
| WO | WO 89/10134 A1 | 11/1989 |
| WO | WO 90/07572 | 7/1990 |
| WO | WO 90/08164 A1 | 7/1990 |
| WO | WO 90/08823 A1 | 8/1990 |
| WO | WO 90/13540 A1 | 11/1990 |
| WO | WO 91/14697 A1 | 10/1991 |
| WO | WO 92/01055 A1 | 1/1992 |
| WO | WO 92/18135 | 10/1992 |
| WO | WO 92/22310 A1 | 12/1992 |
| WO | WO 93/15189 A1 | 8/1993 |
| WO | WO 94/04193 A1 | 3/1994 |
| WO | WO 94/05332 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/28024 A1 | 12/1994 |
| WO | WO 95/02421 A1 | 1/1995 |
| WO | WO 95/04278 A1 | 2/1995 |
| WO | WO 96/11953 A1 | 4/1996 |
| WO | WO 96/40731 | 6/1996 |
| WO | WO 96/21468 A1 | 7/1996 |
| WO | WO 96/21469 A1 | 7/1996 |
| WO | WO 96/32491 | 10/1996 |
| WO | WO 96/36357 A1 | 11/1996 |
| WO | WO 96/40881 A1 | 12/1996 |
| WO | WO 97/05330 | 2/1997 |
| WO | WO 98/05363 | 2/1998 |
| WO | WO 98/31826 | 7/1998 |
| WO | WO 98/41562 A1 | 9/1998 |
| WO | WO 98/51784 A1 | 11/1998 |
| WO | WO 98/58964 | 12/1998 |
| WO | WO 99/00150 A2 | 1/1999 |
| WO | WO 99/14259 A1 | 3/1999 |
| WO | WO 99/22764 A1 | 5/1999 |
| WO | WO 99/34833 A1 | 7/1999 |
| WO | WO 99/45964 A1 | 9/1999 |
| WO | WO 99/48515 A1 | 9/1999 |
| WO | WO 99/55376 A1 | 11/1999 |
| WO | WO 00/23114 | 4/2000 |
| WO | WO 00/26354 A1 | 5/2000 |
| WO | WO 00/65087 | 11/2000 |
| WO | WO 01/02017 A2 | 1/2001 |
| WO | WO 01/05434 A2 | 1/2001 |
| WO | WO 01/39788 A2 | 6/2001 |
| WO | WO 01/49830 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | WO 01/88117 A2 | 11/2001 |
| WO | WO 02/02597 A2 | 1/2002 |
| WO | WO 02/13843 A2 | 2/2002 |
| WO | WO 02/13873 A1 | 2/2002 |
| WO | WO 02/44196 A1 | 6/2002 |
| WO | WO 02/053580 A2 | 7/2002 |
| WO | WO 02/074806 A2 | 9/2002 |
| WO | WO 02/002764 A2 | 10/2002 |
| WO | WO 02/092619 A2 | 11/2002 |
| WO | WO 03/017949 A2 | 3/2003 |
| WO | WO 03/031464 A2 | 4/2003 |
| WO | WO 03/045980 A2 | 6/2003 |
| WO | WO 03/046150 A2 | 6/2003 |
| WO | WO 03/093448 A2 | 11/2003 |
| WO | WO 04/000366 A1 | 12/2003 |
| WO | WO 2004/009838 A2 | 1/2004 |
| WO | WO 2004/010327 A2 | 1/2004 |
| WO | WO 2004/022004 A2 | 3/2004 |
| WO | WO 2004/033651 A2 | 4/2004 |
| WO | WO 2004/046222 A1 | 6/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/096148 A2 | 11/2004 |
| WO | WO 2004/099231 A2 | 11/2004 |
| WO | WO 2004/103275 A2 | 12/2004 |
| WO | WO 2005/012484 A2 | 2/2005 |
| WO | WO 2005/025606 A1 | 3/2005 |

| | | |
|---|---|---|
| WO | WO 2005/051327 A2 | 6/2005 |
| WO | WO 2005/055946 * | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/091944 A2 | 10/2005 |
| WO | WO 2005/121331 A2 | 12/2005 |
| WO | WO 2006/010143 A2 | 1/2006 |
| WO | WO 2006/014349 A2 | 2/2006 |
| WO | WO 2006/014466 A2 | 2/2006 |
| WO | WO 2006/020372 A2 | 2/2006 |
| WO | WO 2006/031811 A2 | 3/2006 |
| WO | WO 2006/050247 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/105426 A2 | 10/2006 |
| WO | WO 2006/121569 A2 | 11/2006 |
| WO | WO 2006/127910 A2 | 11/2006 |
| WO | WO 2007/022512 A2 | 2/2007 |
| WO | WO 2007/056191 A2 | 5/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Brockhausen et al., *Acta Anatomica*, 161: 36-78 (1998).
Cantin et al., *Am. J. Respir. Cell Mol. Biol.*, 27(6): 659-665 (2002).
Cohn et al., *J. Biomed. Mater. Res,*. 22(11): 993-1009 (1988).
Copeland, "Enzymes: A Practical Introduction to Structure, Mechanism and Data Analysis" 2nd ed., Wiley-VCH, New York, pp. 146-150 (2000).
Edge et al., *Anal. Biochem.*, 118(1): 131-137 (1981).
Feldman et al., *Proc. Natl. Acad. Sci. USA*, 102(8): 3016-3021 (2005).
Felix et al., *J. Peptide Res.*, 63: 85-90 (2004).
Ge et al., *J. Biol. Chem.*, 272(34): 21357-21363 (1997).
Gervais et al., *Glycobiology*, 13(3): 179-189 (2003).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Grabenhorst et al., *J. Biol. Chem.*, 274(51): 36107-36116 (1999).
Gross et al., *Biochemistry*, 28(18): 7386-7392 (1989).
Harris (ed.), "Poly(Ethylene Glycol) Chemistry: Biotechnical and Biomedical Applications", Plenum Press, New York (1992).
Harris et al. (eds.), "Poly(ethylene glycol): Chemistry and Biological Applications," ACS Symposium Series, vol. 680, American Chemical Society (1997).
Hassan et al., *Carbohydrates in Chemistry and Biology*, Part II, 3: 273-292 (2000).
Herscovics et al., *FASEB J.*, 7(6): 540-550 (1993).
Kajihara et al., *Carbohydrate Research*, 315: 137-141 (1999).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keene et al., *J. Biol. Chem.*, 264(9): 4769-4775 (1989).
Keppler et al., *Glycobiology*, 11(2): 11R-18R (2001).
Kobayashi et al., *Eur. J. Nucl. Med.*, 27(9):1334-1339 (2000).
Kornfeld et al., *Ann. Rev. Biochem.*, 54: 631-664 (1985).
Kukuruzinska et al., *Proc. Natl. Acad. Sci. USA*, 84(8): 2145-2149 (1987).
Langer, *Science*, 249(4976): 1527-1533 (1990).
Legault et al., *J. Biol. Chem.*, 270(36): 20987-20996 (1995).
Lin et al., *Proc. Natl. Acad. Sci. USA*, 82: 7580-7584 (1985).
Meynial-Salles et al., *J. Biotechnol.*, 46(1): 1-14 (1996).
Min et al., *Endocr. J.*, 43(5): 585-593 (1996).
Muller et al., *J. Biol. Chem.*, 272(40): 24780-24793 (1997).
Muller et al., *J. Biol. Chem.*, 274(26): 18165-18172 (1999).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Orlean, "Vol. III: The Molecular and Cellular Biology of the Yeast Saccharomyces: Cell Cycle and Cell Biology", in *Biogenesis of Yeast Wall and Surface Components*, Chapter 3, pp. 229-362, Cold Spring Harbor Laboratory Press (1997).
Rotondaro et al., *Mol. Biotech.*, 11: 117-128 (1999).
Rudikoff et al., *Proc. Natl. Acad. Sci. USA*, 79(6):1979-1983 (1982).
Sasaki et al., *J. Biol. Chem.*, 262(25): 12059-12076 (1987).
Sasaki et al., *J.Biol. Chem.*, 269: 14730-14737 (1994).
Seely et al., *J. Chromatog.*, 908: 235-241 (2001).
Seitz, *Chembiochem.*, 1(4): 214-246 (2000).
Shen et al., *Biochem. Biophys. Res. Commun.*, 102(3): 1048-1054 (1981).
Shinkai et al., *Prot. Exp. Purif.*, 10: 379-385 (1997).
Snider et al., *J. Chromatogr.*, A 599(1-2): 141-155 (1992).
Sojar et al., *Arch. Biochem. Biophys.*, 259(1): 52-57 (1987).
Srinivasachar et al., *Biochemistry*, 28(6): 2501-2509 (1989).
Stemmer, *Nature*, 370(6488): 389-391 (1994).
Stemmer, *Proc. Natl. Acad. Sci. USA*, 91(22): 10747-10751 (1994).
Strausberg et al., *Proc Natl Acad Sci USA*, 99(26): 16899-16903 (2002).
Taniguchi et al., *Proteomics*, 1(2): 239-247 (2001).
Ten Hagen et al., *J. Biol. Chem.*, 274(39): 27867-27874 (1999).
Tsunoda et al., *J. Pharmacol. Exp. Ther.*, 209(1): 368-372 (1999).
Urdal et al., *J. Chromatogr.*, 296: 171-179 (1984).
Van Reis et al., *Biotechnol. Bioeng.*, 38(4): 413-422 (1991).
Vitetta et al., *Science*, 313: 308-309 (2006).
White et al., *J. Biol. Chem.*, 270(41): 24156-24165 (1995).
Witte et al., *J. Am. Chem. Soc.*, 119(9): 2114-2118 (1997).
Wong et al., *J. Org. Chem.*, 47(27): 5416-5418 (1982).
Wu et al., *J. Drug Target.*, 10(3): 239-245 (2002).
Yamada et al., *Biochemistry*, 20(17): 4836-4842 (1981).
Younes et al., *J. Biomed. Mater. Res.*, 21(11): 1301-1316 (1987).
Zarling et al., *J. Immunol.*, 124(2): 913-920 (1980).
Adelhorst et al., *J. Biol. Chem.*, 269(9): 6275-6278 (1994).
Boime et al., *Recent Prog. Horm. Res.*, 54: 271-289 (1999).
Brockhausen et al., *Glycoconj. J.*, 15: 595-603 (1998).
Broun et al., *Science*, 282(5392): 1315-1317 (1998).
Costa et al., *J. Biol. Chem.*, 272(17): 11613-11621 (1997).
De Vries et al., *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Elhalabi et al., *Curr. Med. Chem.*, 6(2): 93-116 (1999).
Fairhall et al., *Endocrinology*, 131(4): 1963-1969 (1992).
Francis et al., *Intl. J. Hematol.*, 68(1): 1-18 (1998).
Hansen et al., *Biochem J.*, 308: 801-813 (1995).
Haro et al., *Biochem. Biophys. Res. Comm.*, 228(2): 549-556 (1996).
Höglund, *Med. Oncol.*, 15(4): 229-233 (1998).
Jezek et al., *J. Peptide Sci.*, 5: 46-55 (1999).
Kaneko et al., *Cytogenet. Cell Genet.*, 86(3-4): 329-330 (1999).
Kaneko et al., *FEBS Lett.*, 452(3): 237-242 (1999).
Kimura et al., *Proc. Natl. Acad. Sci. USA*, 96(8): 4530-4535 (1999).
Kisselev, *Structure*, 10(1): 8-9 (2002).
Kukowska-Latallo et al., *Genes Dev.*, 4(8): 1288-1303 (1990).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lönnberg, *Curr. Org. Synth.*, 6(4): 400-425 (2009).
Malissard et al., *Biochem. Biophys. Res. Commun.*, 267(1): 169-173 (2000).
Mollicone et al., *Eur. J. Biochem.*, 191(1): 169-176 (1990).
Monaco et al., *Gene*, 180: 145-150 (1996).
Nagata et al., *EMBO J.*, 5(3): 575-581 (1986).
Nunez et al., *Can. J. Chem.*, 59(14): 2086-2095 (1981).
Oh-Eda et al., *J. Biol. Chem.*, 265: 11432-11435 (1990).
Orskov et al., *J. Biol. Chem.*, 264(22): 12826-12829 (1989).

Palcic et al., *Carbohydr. Res.*, 190(1): 1-11 (1989).
Prati et al., *Biotech and Bioeng.*, 79(5): 580-585 (2002).
Prieels et al., *J. Biol. Chem.*, 256(20): 10456-10463 (1981).
Rasko et al., *J. Biol. Chem.*, 275(7): 4988-4994 (2000).
Seffernick et al., *J. Bacteriol.*, 183(8): 2405-2410 (2001).
Sinclair et al., *J. Pharm. Sci.*, 94: 1626-1635 (2005).
Staudacher, *Trends Glycosci. Glycotechnol.*, 8(44): 391-408 (1996).
Trottein et al., *Mol. Biochem. Parasitol.*, 107(2): 279-287 (2000).
Van Tetering et al., *FEBS Lett.*, 461(3): 311-314 (1999).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(34): 24575-24584 (1992).
Wishart et al., *J. Biol. Chem.*, 270(45): 26782-26785 (1995).
Witkowski et al., *Biochemistry*, 38(36): 11643-11650 (1999).
Witte et al., *Cancer and Metastasis Rev.*, 17: 155-161 (1998).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.

Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.

Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Culajay et al., *Biochem.*, 39: 7153-7158 (2000).
Espuelas et al.,*Bioorg. Med. Chem. Lett.*, 13(15): 2557-2560 (2003).
Hu et al., *Mol. Cell. Biol.*, 18(10): 6063-6074 (1998).
Karkas et al., *J. Biol. Chem.*, 239(4): 949-957 (1964).
Manzi et al. (*J. Biol. Chem.*, 269(38): 23617-23624 (1994).
Natsuka et al., *J. Biol. Chem.*, 269(24): 16789-16794 (1994).
R & D Systems, Fibroblast Growth Factors (FGFs), Internet page from www.rndsystems.com/mini_review_detail_objectname_MR01_FGFs.aspx, 2001, printed Mar. 10, 2011.
Saxon et al., *J. Am. Chem. Soc.*, 124(50): 14893-14902 (2002).
Veronese, *Biomaterials*, 22(5): 405-417 (2001).
Weston et al., *J. Biol. Chem.*, 267(6): 4152-4160 (1992).
Zhang et al., *Biochim. Biophys. Acta*, 1425: 441-452 (1998).
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Amgen, Inc., Prescribing Information for NEUPOGEN® (Sep. 2007).
Brumeanu et al., *J. Immunol. Meth.*, 183: 185-197 (1995).
Deacon, *Diabetes*, 54: 2181-2189 (2004).
Floel et al., *PLOS One* 6(5): e19767. doi:10.1371/journal.pone.0019767 (2011).
Gross et al., *Eur. J. Biochem,.* 177(3): 583-589 (1988).
Guo et al., *Appl. Biochem. Biotechnol.*, 68(1-2): 1-20 (1997).
Hällgren et al., *J. Carb. Chem.*, 14(4-5):453-464 (1995).
Kennedy, "Hydrophobic-Interaction Chromatography," in *Current Protocols in Protein Science*, pp. 8.4.1-8.4.21, Wiley (1995).
Krystal et al., *Blood*, 67(1): 71-99 (1986).
O'Shannessy et al., *J. Appl. Biochem.*, 7: 347-355 (1985).
Quelle et al., *Blood*, 74(2): 652-657 (1989).
Rathnam et al., *Biochim. Biophys. Acta*, 624(2): 436-442 (1980).
Schwarz et al., *Nucl. Med. Biol.*, 26(4):383-388 (1999).
Solaroglu et al., *Stroke*, 37: 1123-1128 (2006).
Srivastava et al., *J. Biol. Chem.*, 267(31): 22356-22361 (1992).
Tom et al., *AAPS Journal*, 9(2): E227-E234 (2007).
Uptima, Detergents: Solubilization of Biomolecules, Internet page from www.interchim.com/interchim/bio/produits_uptima/product_line/p1p_detergents.htm, 2001, printed Nov. 14, 2011.
Yin et al., *Pharm. Res.*, 21(12): 2377-2383 (2004).
Abeijon et al., 1986, J. Biol. Chem. 261(24):11374-11377.
Abuchowski et al., 1977, J. Biol. Chem. 252:3578-3581.
Abuchowski et al., 1977, J. Biol. Chem. 252:3582-3586.
Abuchowski et al., 1984, Cancer Biochem. Biophys. 7:175-186.
Ailor et al., 2000, Glycobiology 10:837-847.
Alam et al., 1998. Journal of Biotechnology. 65: 183-190.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Bedard et al., 1994, Cytotechnology 15:129-138.
Bennett et al., 1998, J. Biol. Chem. 273:30472-30481.
Bennett et al., 1999, FEBS Letters 460:226-230.
Berger et al., 1988, Blood 71:1641-1647.

Berg-Fussman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bork (2000) Genome Research 10:398-400.
Bork et al. (1996) Trends in Genetics 12(10): 425-427.
Bouizar et al., 1986, Eur. J. Biochem. 155:141-147.
Boyd et al., 1995, Mol. Immunol. 32:1311-1318.
Brenner (1999) Trends in Genetics 15(4) 132-133.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Grout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Doerks et al. (1998) Trends in Genetics 14(6): 248-250.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Fritz et al., 2004, PNAS 101(43):15307-15312.
Fritz et al., 2006, J. Biol. Chem. 281(13):8613-8619.
Garnett et al., 2002, Advanced Drug Delivery Reviews 53:171-216.
Gatot, et al., 1998, J. Biol. Chem., 273(21):12870-12880.
Gilbert et al., 1996, Cytotechnology 22:211-216.
Gillis et al., 1988, Behring Inst. Mitt. August 83:1-7.
Ginns, Dr. Edward, PEG Glucocerebrosidase, Internet page from www.gaucher.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hagen et al., 1999, J. Biol. Chem. 274:27867-27874.
Hagen et al., 1999, J. Biol. Chem. 274:6797-6803.
Hagen et al., 2001, J. Biol. Chem. 276:17395-17404.
Hall et al., 2001, Methods in Molecular Biology 166:139-154.
Hang et al., 2001, J. Am. Chem. Soc. 123:1242-1243.
Harris et al., 2003, Nature Reviews Drug Discovery, 2:214-221.
Harris et al., Abstracts of Papers of the American Chemical Society, 1991, V 201, APR, P 64-POLY, p. 154-155.
Harris, 1985, Macronol. Chem. Phys. C25: 325-373.
Hassan et al., 2000, J. Biol. Chem. 275:38197-38205.
Hayes et al., 1993, J. Biol. Chem. 268(22):16170-16178.
Hellstrom et al., 2001, Methods in Molecular Biology 166:3-16.

Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hink et al., 1991, Biotechnology Progress 7:9-14.
Hollister et al., 2001, Glycobiology 11:1-9.
Hounsell et al., 1996, Glycoconj. J. 13:19-26.
Ichikawa et al., 1992, J. Am. Chem. Soc. 114:9283-9298.
Ikonomou et al., 1991, In Vitro Cell. Dev. Biol.-Animal 37:549-559.
Inlow, et al., 1989, J. Tissue Culture Meth. 12:13-16.
Inoue et al., 1995, Biotechnology Annual Review 1:297-313.
Ito et al., 1993, Pure & Appl. Chem. 65(4):753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lau et al. (1999) Journal of Biotechnology 75:105-115.
Lee et al., 1989, Biochemistry 28:1856-1861.
Lee-Huang et al., 1984, Proc. Natl. Acad. Sci. U.S.A. 81:2708-2712.
Leung, S., 1995, J. Immunology, 154:5919-5926.
Li et al., 2002, Trends in Pharmacological Sciences 23:206-209.
Li et al., 2002, Medicinal Research Reviews 22:225-250.
Licari P. et al., 1992, Biotechnology and Bioengineering 39(4):432-441.
Licari P. et al., 1992, Biotechnology and Bioengineering 39(9):932-944.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Journal of Biotechnology 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
Ngo et al. (1994) "The Protein Folding Problem and Tertiary Structure Prediction, Chapter 14: Computational Complexity Protein Structure Prediction, and the Levinthal Paradox" pp. 433-440 and 492-495.
Nilsson et al., 1984, Methods Enzymol. 104:56-69.
O'Connell et al., 1992, J. Biol. Chem. 267:25010-25018.
Oetke, et al., 2002, J. Biol. Chem 277(8):6688-6695.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Plummer et al., 1995, J. Biol. Chem. 270(22):13192-13196.
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Reis et al., 1991, Biotechnology and Bioengineering 38:413-422.
Rosenthal, et al., 1994, Methods Enzymol. 235:253-285.
Sadler et al., 1982, Methods in Enzymology 83:458-514.
Sandberg et al., 2000, Seminars in Hematology 38(2):4-12.
Saneyoshi et al., 2001, Biology of Reproduction 65:1686-1690.
Saxon et al., 2000, Science 287:2007-2010.
Schlaeger, E., 1996, Cytotechnology 20:57-70.
Schwientek et al., 1994, Gene 145:299-303.
Schwientek et al., 2002, J. Biol. Chem. 277:22623-22638.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Skolnick et al. (2000) Trends in Biotech. 18(1): 34-39.
Smith et al. (1997) Nature Biotechnology 15:1222-1223.
Song et al., 2002, J. Pharmacol. Exp. Ther. 301:605-610.
Srinivasachar et al., 1989, Biochemistry 28:2501-2509.
Stephens et al., 1983, European J. of Biochem., 133(1):155-62.
Stephens et al., 1983, European J. of Biochem., 133(3):481-9.
Stephens et al., 1983, European J. of Biochem., 135(3):519-27.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Tenno et al., 2002, J. Biol. Chem. 277(49):47088-96.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Wells (1990) Biochemistry 29(37): 8509-8517.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly(ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.
Office Action dated Mar. 17, 2011 in U.S. Appl. No. 11/597,258.
Office Action dated May 31, 2011 in U.S. Appl. No. 11/144,223.
Office Acton dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Acton dated Aug. 17, 2011 in U.S. Appl. No. 11/632,005.
Office Acton dated Aug. 22, 2011 in U.S. Appl. No. 11/659,942.
Office Action dated Sep. 22, 2011 in U.S. Appl. No. 12/820,926.

Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.

* cited by examiner

LIQUID FORMULATION OF G-CSF CONJUGATE

CROSS-REFERENCE TO RELATED APPLICATIONS

The present application claims priority to U.S. Provisional Patent Application No. 60/968,735, filed on Aug. 29, 2007, the disclosure of which is incorporated herein by reference in its entirety for all purposes.

FIELD OF THE INVENTION

The present invention relates to a liquid pharmaceutical composition comprising a granulocyte colony stimulating factor (G-CSF) polypeptide conjugated to a polymer. The composition shows a good storage stability and is especially useful for the prophylaxis and treatment of disorders and medical indications where granulocyte colony stimulating factor preparations are considered as useful remedies.

BACKGROUND OF THE INVENTION

Granulocyte colony stimulating factor (G-CSF) is a hematopoietic growth factor that stimulates the proliferation and differentiation of hematopoietic precursor cells and the activation of mature neutrophils. G-CSF is capable of supporting neutrophil proliferation in vitro and in vivo. The human form of G-CSF was cloned by groups from Japan and the USA in 1986 (see e.g. Nagata et al. (1986) Nature 319: 415-418). The natural human glycoprotein exists in two forms, one having 174 and the other having 177 amino acids. The more abundant and more active 174 amino acid form has been used in the development of pharmaceutical products by recombinant DNA technology.

Large quantities of recombinant G-CSF have been produced in genetically engineered *Escherichia coli* and have been successfully used in clinical applications to treat cancer patients suffering from chemotherapy-induced neutropenia. *Escherichia coli*-produced G-CSF is a 175 amino acid polypeptide chain containing an extra methionine at its N-terminus. This protein has been produced by expressing a G-CSF gene in *E. coli* and purifying the protein product to homogeneity. It is a hydrophobic protein that has five cysteine residues, four of them are involved in disulfide bonding. The free cysteine residue is generally implicated in the formation of higher molecular weight aggregates upon storage in solution. Aggregates of the proteins can also be formed from oxidized forms of the protein that arise by oxidation of the internal methionine residues in the primary sequence of the protein. Of the four methionine residues, one is at the N-terminus and the other three are internal. The oxidized forms of the protein containing oxidized methionine at position 122 can be separated from the native protein and the forms containing oxidized methionine at positions 127 or 138 by reverse phase HPLC separation procedures (the positions are calculated for the methionyl-G-CSF consisting of 175 amino acids).

Filgrastim is a recombinant human G-CSF synthesized in an *E. coli* expression system (international non-proprietary name, INN). The structure of filgrastim differs slightly from that of the natural glycoprotein. Lenograstim (INN) is another form of recombinant human G-CSF and is synthesized in Chinese hamster ovary (CHO) cells. Filgrastim and lenograstim are marketed in Europe under the trade names Neupogen® and Granocyte, respectively. The commercially available forms of recombinant human G-CSF have a short-lived pharmacological effect and often must be administered more than once a day for the duration of the leukopenic state.

Protein-engineered variants of human G-CSF are known, e.g. those described in WO 01/87925, EP 0 456 200 A, U.S. Pat. No. 6,166,183, U.S. Pat. No. 6,004,548, U.S. Pat. No. 5,580,755, U.S. Pat. No. 5,582,823, U.S. Pat. No. 5,675,941, U.S. Pat. No. 5,416,195, U.S. Pat. No. 5,399,345, WO 2005/055946 and WO 2006/074467.

Modification of human G-CSF and other polypeptides so as to introduce at least one carbohydrate chain in addition to those in the native polypeptide has also been reported (U.S. Pat. No. 5,218,092).

In general, the stability of proteins can be improved and the immune response against these proteins reduced when these proteins are coupled to polymeric molecules. WO 94/28024 discloses that physiologically active proteins modified with PEG exhibit reduced immunogenicity and antigenicity and circulate in the bloodstream considerably longer than unconjugated proteins, i.e. have a reduced clearance rate.

The attachment of synthetic polymers to the peptide backbone to improve the pharmacokinetic properties of glycoprotein therapeutics has been explored. An exemplary polymer conjugated to peptides is PEG. The use of PEG to derivatize peptide therapeutics can reduce the immunogenicity of the peptides. For example, U.S. Pat. No. 4,179,337 discloses non-immunogenic polypeptides such as enzymes and peptide hormones coupled to PEG or poly(propylene glycol) (PPG). In addition to reduced immunogenicity, the clearance time in circulation of PEG-modified polypeptides is prolonged due to the increased size of the PEGylated polypeptide conjugate.

In addition, polymer modifications of native human G-CSF, including attachment of poly(ethylene glycol) (PEG) groups, has been reported (see, e.g., U.S. Pat. No. 5,824,778, U.S. Pat. No. 5,824,784, WO 96/11953, WO 95/21629 and WO 94/20069). Pegfilgrastim (INN) is a covalent conjugate of recombinant methionyl human G-CSF (filgrastim) and a single 20 kDa monomethoxy-PEG-molecule. The monomethoxy-PEG-molecule is covalently bound to the N-terminal methionyl residue of filgrastim. Pegfilgrastim is marketed in Europe under the trade name NEULASTA®.

The principal mode of attachment of PEG, and its derivatives, to peptides is a non-specific bonding through a peptide amino acid residue (see e.g. U.S. Pat. No. 4,088,538, U.S. Pat. No. 4,496,689, U.S. Pat. No. 4,414,147, U.S. Pat. No. 4,055, 635 and WO 87/00056). Another mode of attaching PEG to peptides is through the non-specific oxidation of glycosyl residues on a glycopeptide (see e.g. WO 94/05332).

In these art-recognized methods, PEG is added in a random, non-specific manner to reactive residues on a peptide backbone. Random addition of PEG molecules has its drawbacks, including a lack of homogeneity of the final product, and the possibility that the biological or enzymatic activity of the peptide will be reduced. Therefore, efforts have been made to develop more site specific methods for attaching a synthetic polymer or other label to a peptide and it has been found that specifically conjugated, homogeneous peptide therapeutics can be produced in vitro through the action of enzymes. These enzyme-based conjugation strategies have the advantages of regioselectivity and stereoselectivity. Two principal classes of enzymes used in the synthesis of conjugated peptides are glycosyltransferases (e.g. sialyltransferases, oligosaccharyltransferases, N-acetylglucosaminyltransferases) and glycosidases. These enzymes specifically attach substrate sugars to polypeptides, which can be subsequently modified with a polymer or other moiety. Alternatively, glycosyltransferases and modified glycosidases can be used to directly transfer modified sugars to a peptide backbone (see e.g. U.S. Pat. No. 6,399,336 and US 2003/0040037, US 2004/0132640, US 2004/0137557, US 2004/0126838 and US 2004/0142856). Methods combining both chemical and enzymatic synthetic elements are also known (see e.g. US 2004/137557).

Various methods of conjugating polypeptides like G-CSF with polymeric moieties like PEG are described in the art. The preparation of glycoPEGylated G-CSF is, for example, described in WO 2005/055946. WO 2006/074467 describes the preparation of conjugates between G-CSF and PEG moieties. In this method the conjugates are linked via an intact glycosyl linking group, which is interposed between and covalently attached to the G-CSF polypeptide and the PEG moiety. The conjugates are formed from both glycosylated and unglycosylated G-CSF polypeptides by the action of a glycosyltransferase on a PEGylated substrate nucleotide sugar. The glycosyltransferase ligates a modified sugar moiety onto either an amino acid or glycosyl residue on the polypeptide. The disclosure of WO 2005/055946 and WO 2006/074467 are explicitly incorporated herein by reference in their entirety for all purposes.

Besides PEG, other polymeric moieties are useful conjugation partners with G-CSF. For example, WO 02/09766 discloses, inter alia, biocompatible protein-polymer compounds produced by conjugation of biologically active protein with a biocompatible polymer derivative. The biocompatible polymer is a highly reactive branched polymer, and the resulting conjugates contain a long linker between the polymer and polypeptide. Examples of biocompatible polymers according to WO 02/09766 are PEG, PPG, polyoxyethylene (POE), polytrimethylene glycol, polylactic acid and its derivatives, polyacrylic acid and its derivatives, polyamino acids, polyurethane, polyphosphazene, poly(L-lysine), polyalkylene oxide (PAO), water-soluble polymers such as polysaccharide, dextran, and non-immunogenic polymers such as polyvinyl alcohol and polyacryl amide.

WO 96/11953 describes N-terminally chemically modified protein compounds and methods for their production. Specifically, G-CSF compositions are described which result from coupling a water-soluble polymer to the N-terminus of G-CSF. Examples of water-soluble polymers listed in WO 96/11953 are copolymers of ethylene glycol and propylene glycol, carboxymethyl cellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, PPG homopolymers, polypropylene oxide/ethylene oxide copolymers or polyoxyethylated polyols.

WO 97/30148 describes polypeptide conjugates with reduced allergenicity, comprising a polymeric carrier molecule having two or more polypeptide molecules coupled thereto. These conjugates are produced by activating a polymeric carrier molecule, reacting two or more polypeptide molecules with the activated polymeric carrier molecule and blocking of residual active groups on the conjugate. This publication lists a variety of polymeric carrier molecules, including natural or synthetic homopolymers such as polyols, polyamines, polycarboxylic acids and heteropolymers comprising at least two different attachment groups.

WO 03/074087 relates to a method of coupling proteins to a starch-derived modified polysaccharide. The binding between the protein and the polysaccharide, hydroxyalkyl starch, is a covalent linkage which is formed between the terminal aldehyde group or a functional group resulting from chemical modification of the terminal aldehyde group of the starch molecule and a functional group of the protein. Disclosed protein reactive groups include amino groups, thio groups and carboxy groups.

WO 2005/014050 describes the preparation of conjugates of hydroxyalkyl starch (HAS) and a G-CSF protein, wherein at least one functional group of the reacts with at least one functional group of the protein, thereby forming a covalent linkage. Other documents disclosing HASylation, e.g., HESylation, of polypeptides include WO 2005/014655, WO 2005/092390, WO 2007/031266, WO 2005/092928 and WO 2005/092391.

Although approaches for modifying therapeutic polypeptides such as G-CSF with polymeric moieties to prolong polypeptide clearance time and to reduce immunogenicity, scant literature is available regarding developing advantageous formulations for such polymer-G-CSF-conjugates.

The above mentioned NEULASTA® (pegfilgrastim) product is a liquid composition intended for subcutaneous injection. The preparation comprises pegfilgrastim, sodium acetate, sorbitol, polysorbate 20 and water for injection and has a pH of 4.0 (see www.neulasta.com, and ROTE LISTE 2007). The NEULASTA® (pegfilgrastim) and NEUPOGEN® (filgrastim) products, both marketed by Amgen, are almost identical with respect to buffer agent, excipients and pH value of the solution: NEUPOGEN® comprises filgrastim (instead of pegfilgrastim), sodium acetate, sorbitol, polysorbate 80 and water for injection with a pH of 4.0 (see www-.neupogen.com, and ROTE LISTE 2007).

Although some pharmaceutical compositions developed for non-conjugated G-CSF are presented in the patent literature in such a way as to encompass preparations in which the non-conjugated G-CSF is replaced by a PEG-G-CSF conjugate, it is obvious that the compositions are tailored to, and tested for, unconjugated G-CSF only. These references do not disclose the formulation of a glycoPEGylated G-CSF conjugate.

For example, WO 2005/042024 describes stable pharmaceutical compositions comprising G-CSF having a pH value above 4.0 and further comprising an acid. The composition is free from surfactants. The pharmaceutical composition described in WO 2005/042024 was developed for non-conjugated G-CSF; however, mention is made of its use with G-CSF chemically modified with a polymer, showing the same or improved biological activity.

Another example is WO 2005/039620 which is directed to a stable aqueous G-CSF containing composition. The composition contains succinic acid or tartaric acid or salts thereof as buffer agents and has a preferred pH in the range of 4.0 and 5.8. According to the specification, the G-CSF protein may also be synthetically modified, e.g. by enzymatic glycosylation or chemical PEGylation.

EP 1 260 230 A1 discloses stable protein formulations containing tryptophan as a stabilizer. The list of proteins covers G-CSF, and G-CSF chemically modified with PEG or the like as well. The G-CSF formulations are mentioned as preferably having a pH of 5-7, more preferably 6.0-6.7.

Another example is EP 1 336 410 A1, which describes injectable pharmaceutical formulations containing a physiologically active protein as an active ingredient and at least one sugar as a soothing agent and a pH of 6.5-7.4.

EP 1 329 224 A1 describes a G-CSF solution formulation containing at least one amino acid or a salt thereof, preferably methionine, as a stabilizer. The G-CSF solution formulations preferably have a pH of 5-7, more preferably 5.5-6.8. G-CSF chemically modified with PEG or the like is said to be also included.

The formulations described in the patent literature have only been developed and tested for unconjugated G-CSF. Though exemplary references disclosing G-CSF formulations mention the use of the formulation with a polymeric conjugate of G-CSF or a generic PEG-G-CSF conjugate, none of the references describe a formulation of a polymeric G-CSF having a particular structure.

The problem underlying the present invention is to provide a polymer-G-CSF conjugate formulation which is particularly adapted to such conjugates and which is stable at elevated temperatures, generally, above refrigerator temperature (e.g., between about 2 and about 8° C.). Further, it is an object of the invention to provide a pharmaceutical composition which does require reconstitution at any stage of its preparation and which causes as little irritation as possible when administered to a patient.

SUMMARY OF THE INVENTION

These problems are solved by the present invention by providing a aqueous pharmaceutical formulation comprising a polymer-G-CSF conjugate. Exemplary formulations according to the present invention have a pH in the range of 4.5 to 5.5. The aqueous formulation according to the invention comprises a surfactant and optionally one or more other pharmaceutically acceptable excipient. In various embodiments, the formulation is free of amino acids or derivatives or salts thereof as stabilizers. In some embodiments, the formulations are free from organic acids and salts thereof. In various exemplary embodiments, the formulations are free from tartaric acid or salts thereof and/or succinic acid or salts thereof as a buffering agent. In an exemplary embodiment, the formulation is free of amino acids, succinic acid and tartaric acid and derivatives and salts of these formulations.

It has surprisingly been found that formulating a polymer-G-CSF conjugate in a composition having a pH value in the range of from about 4.5 to about 5.5 prevents acid hydrolysis of the conjugate bond. An exemplary formulation has a pH of about 5.0. The pH range of the formulations of the invention improves the stability of the solution at temperatures above refrigerator temperature (2-8° C.), especially at room temperature (i.e. below 25° C.) and even at higher temperatures, e.g. 40° C. Thus, the G-CSF conjugate formulations of the invention can be stored without cooling for a prolonged period of time, without significant loss of activity and without significant degradation.

Further, irrespective of storage stability, the compositions according to the invention are advantageous over a comparable composition having a pH of 4.0, since a composition which is less acidic causes less irritation when administered to a patient.

Other objects, advantages and aspects of the present invention are apparent from the detailed description that follows.

DETAILED DESCRIPTION OF THE INVENTION

Definitions

Unless otherwise indicated, the following definitions are set forth to illustrate and define the meaning and scope of the various terms used to describe the invention herein.

The term "polymer-G-CSF conjugate" refers to a conjugate between a G-CSF polypeptide and a polymer wherein the conjugate is formed by a covalent linkage between a functional group of the polymer and a functional group of the polypeptide. The conjugates may comprise one or more polymeric moieties. An exemplary polymer is a poly(alkylene oxide), e.g., PEG.

The term "G-CSF" (or G-CSF polypeptide or G-CSF protein or G-CSF peptide) refers to a protein having the in vivo biological activity of naturally occurring human G-CSF, i.e. a protein that is capable of stimulating the differentiation and proliferation of hematopoietic progenitor cells. The G-CSF can be unmistakably identified as G-CSF according to the assay described in Stute, N., et al. "Pharmacokinetics of subcutaneous recombinant human granulocyte colony-stimulating factor in children" (1992) Blood 79 (11), pages 2849-2854.

In an exemplary embodiment, G-CSF has an amino acid sequence according to the following SEQ ID NO:1 or SEQ ID NO:2, wherein SEQ ID NO:1 depicts the wild type amino acid sequence of human methionyl-G-CSF as produced in *E. coli*, and SEQ ID NO:2 depicts the amino acid sequence of human G-CSF as produced in mammalian cells, e.g. in CHO cells. SEQ ID NO:1 is the 175 amino acid variant, wherein the first amino acid is methionine and there is a threonine residue at Thr 134. SEQ ID NO:2 is a 174 amino acid variant which has the same sequence as the 175 amino acid variant except the leading methionine is missing, thus the sequence begins with T and there is a Threonine residue at position 133.

```
SEQ ID NO:1:
MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPALQPTQGAMPAFASAFQRRAG

GVLVASHLQSFLEVSYRVLRHLAQP (175 amino acids)

SEQ ID NO:2
TPLGPASSLPQSFLLKCLEQVRKIQGDGAALQEKILCATYKILCHPEELVL

LGHSLGIPWAPLSSCPSQALQLAGCLSQLHSGLFLYQGLLQALEGISPELG

PTLDTLQLDVADFATTIWQQMEELGMAPALQPTQGAMPAFASAFQRRAGGV

LVASHLQSFLEVSYRVLRHLAQP (174 amino acids)
```

The skilled artisan will readily appreciate that the present invention is not limited to the sequences depicted herein, but also includes variants of G-CSF. Such variants are well known in the art. They may contain deletions, substitutions or additions of one or more amino acids in the above depicted amino acid sequences while maintaining the biological activity of naturally occurring G-CSF. As examples, but in no way meant to be limiting to the present invention, G-CSF variants are described in WO 01/87925, EP 0 456 200 A, U.S. Pat. No. 6,166,183, U.S. Pat. No. 6,004,548, U.S. Pat. No. 5,580,755, U.S. Pat. No. 5,582,823, U.S. Pat. No. 5,675,941, U.S. Pat. No. 5,416,195, U.S. Pat. No. 5,399,345, WO 2005/055946 and WO 2006/074467.

The G-CSF polypeptide may be glycosylated or non-glycosylated. In an exemplary embodiment, the G-CSF polypeptide is recombinant human G-CSF produced in *E. coli*, i.e. having the amino acid sequence depicted above in SEQ ID NO:1 or a variant thereof.

The polymer can be any polymer that can be covalently linked to the G-CSF polypeptide, either directly or through a linker, and which results in a therapeutically useful polymer-G-CSF-conjugate, when covalently linked to a G-CSF polypeptide. Several suitable polymers have already been mentioned above in the introductory sections of this application; these include poly(alkylene glycols), e.g., PEG and PPG, hydroxyalkyl starches, e.g., hydroxyethyl starch (HES), and the polymers described in WO 02/09766, WO 96/11953 and WO 97/30148 in connection with polymeric polypeptide conjugates. In an preferred embodiment the polymer is PEG.

"Poly(alkylene oxide)" refers to a genus of compounds having a polyether backbone. Poly(alkylene oxide) species in the G-CSF conjugates formulated according to the present invention include, for example, straight- and branched-chain species. Moreover, exemplary poly(alkylene oxide) species can terminate in one or more reactive, activatable, or inert groups. For example, poly(ethylene glycol) is a poly(alkylene oxide) consisting of repeating ethylene oxide subunits, which may or may not include additional reactive, activatable or inert moieties at either terminus. Exemplary poly(alkylene oxide) species include those in which one terminus is "capped" by an inert group, e.g., monomethoxy-poly(alkylene oxide), particularly monomethoxy-poly(ethylene oxide). When the molecule is a branched species, it may include multiple reactive, activatable or inert groups at the termini of the alkylene oxide chains and the reactive groups may be either the same or different.

The term "PEG-G-CSF" (PEGylated-G-CSF) refers to a G-CSF protein which is covalently linked with one or more polyethylene glycol moieties as described below. The PEG group(s) and the G-CSF protein may be either linked to each other directly or via a linker, e.g. a glycosyl linking group.

As used herein, the term "modified sugar," refers to a naturally- or non-naturally-occurring carbohydrate component of a G-CSF conjugate in a formulation of the invention. In various embodiments, the modified sugar is one that is enzymatically transferred onto an amino acid or a glycosyl residue of a G-CSF peptide to form the conjugate in the formulation of the invention. In these embodiments, the modified sugar is derived from an enzymatically transferable saccharide substrate including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a polymer, e.g., PEG.

The term, "glycosyl linking group," as used herein refers to a glycosyl residue to which a polymer, e.g., a PEG moiety is covalently attached to a G-CSF peptide; the glycosyl linking group joins the polymer to the remainder of the conjugate. In various formulations of the invention, the "glycosyl linking group" is covalently attached to a glycosylated or unglycosylated peptide, thereby linking the agent to an amino acid and/or glycosyl residue on the peptide. In various embodiments, the formulation includes a G-CSF conjugate in which the glycosyl linking group is a saccharide-derived structure that is degraded during formation of a modified sugar (e.g., saccharide oxidation→Schiff base formation→reduction). In certain exemplary embodiments, the glycosyl linking group is intact. An "intact glycosyl linking group" refers to a modified sugar that is derived from a glycosyl moiety in which the saccharide monomer that links the polymer to the G-CSF of the conjugate is not degraded, e.g., oxidized, e.g., by sodium metaperiodate. An exemplary form of degradation is a loss of one or more carbon atoms from a naturally occurring saccharide structure. "Intact glycosyl linking groups" in G-CSF conjugates in formulations of the invention can be derived from a naturally occurring oligosaccharide by addition of glycosyl unit(s) or removal of one or more glycosyl unit from a parent saccharide structure.

THE EMBODIMENTS

All concentration specifications in mg/mL used in the following in connection with the conjugate are related to the G-CSF moiety only. The polymer, e.g., PEG, moiety by definition is not considered for the mass concentration.

While filgrastim has a molecular weight of about 18-19 kD, pegfilgrastim is much larger due to the monomethoxy-PEG moiety and has a molecular weight of about 39 kD. In various embodiments, the polymer-G-CSF-conjugates in the formulations of the present invention may have a molecular weight in the range of 20 to 60 kD, preferably in the range of 35 to 45.

When the G-CSF conjugate in the formulation of the invention is a PEG conjugate, essentially any PEG molecule recognized in the art can be a component of the conjugate. Exemplary PEGs in conjugates formulated according to the invention are disclosed in, e.g. in WO 2005/055946, WO 2006/074467 and WO 01/87329. The PEG moiety may be linear or branched. Exemplary PEG moieties in the formulated G-CSF conjugates have a molecular weight of from about 5 kD to about 40 kD. In various embodiments, a PEG moiety has a molecular weight of from about 15 kD to about 25 kD. In an exemplary embodiment, a PEG moiety in a G-CSF conjugate in a formulation of the invention has a molecular weight of about 20 kD.

Methods for producing polymer-G-CSF-conjugates, e.g., those in the formulations of the invention are known. Accordingly, the documents mentioned above in connection with the preparation of conjugates between polypeptides and polymeric moieties are incorporated herein by reference in their entirety for all purposes.

Other polymer-G-CSF-conjugates which are found in formulations of the present invention are described in detail in WO 96/11953, EP 822 199 A, WO 01/51510, WO 2006/0128460, EP 921 131 A and EP 744 409, each of which is incorporated herein by reference in its entirety for all purposes.

The skilled artisan will readily appreciate that the present invention is not limited to conjugates wherein a polymer, e.g., PEG or HES is directly linked to an amino acid residue of the protein, but also encompasses conjugates wherein a polymeric moiety and the G-CSF polypeptide are linked to each other via a linker. For example, glycosyl linking groups interposed between the polypeptide and the PEG moieties are useful linkers within the conjugates in the formulations of the present invention. WO 2006/074467 describes such polymer-G-CSF conjugates in which the G-CSF polypeptide and the polymeric moiety are linked via a glycosyl linker or via a non-glycosyl linker, e.g. substituted or unsubstituted alkyl, substituted or unsubstituted heteroalkyl. The disclosure of WO 2006/074467 is explicitly incorporated by reference herein in its entirety for all purposes.

In one embodiment of the present invention the polymer-G-CSF peptide conjugate is prepared according to the method described in WO 2006/074467. In a preferred embodiment the polymer-G-CSF peptide is a PEG-G-CSF conjugate having a glycosyl linking group interposed between the PEG modifying moiety and the G-CSF polypeptide. Such a conjugate is referred to as "glycoPEGylated" G-CSF.

In an exemplary embodiment, "glycopeglyated" G-CSF molecules of the invention are produced by the enzyme mediated formation of a conjugate between a glycosylated or non-glycosylated G-CSF peptide and an enzymatically transferable saccharyl moiety that includes a poly (ethylene glycol) moiety within its structure. The PEG moiety is attached to the saccharyl moiety directly (i.e., through a single group formed by the reaction of two reactive groups) or through a linker moiety, e.g., substituted or unsubstituted alkyl, substituted or unsubstituted heteroalkyl, etc. The glycosyl linking group may be sialic acid moieties that are derivatized with PEG.

In a preferred embodiment of the invention the glycosyl linker is bound to the G-CSF protein via O-glycosylation, preferably via O-glycosylation at a threonine residue of the G-CSF protein.

The glycosyl linker preferably comprises a mono-, di- or oligosaccharide, more preferably the glycosyl linker comprises sialic acid and N-acetylgalactosamine.

In various formulations of the present invention the polymer-G-CSF peptide conjugate comprises the sialic acid moiety:

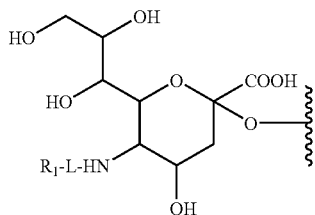

(I)

wherein $R_1$ is a polymer, e.g., a moiety comprising a straight-chain or branched poly(alkylene glycol) residue, e.g., a PEG; and L is a linker which is a member selected from a bond, substituted or unsubstituted alkyl and substituted or unsubstituted heteroalkyl. In an exemplary embodiment, the moiety is covalently bound to a glycosyl residue on the G-CSF peptide. In various embodiments, the glycosyl residue is N-acetylgalactosamine.

In an exemplary embodiment, the glycosyl residue is bound to a threonine residue of the G-CSF peptide. Exemplary threonine residues at which the G-CSF conjugates of the invention are glycosylated include the threonine at position 134 (calculated for the methionyl-G-CSF polypeptide, i.e. having an N-terminal methionine and 175 amino acids in total).

In an exemplary embodiment, the sialic acid moiety shown above is bound to a N-acetylgalactosamine residue which is bound to a threonine at position 134 (calculated for the methionyl-G-CSF polypeptide, i.e. having an N-terminal methionine and 175 amino acids in total).

In an exemplary embodiment according to the description above, the PEG moiety attached to the sialic acid moiety, $R_1$ is a straight-chain poly(ethylene glycol) residue, and L is a heteroalkyl moiety. An exemplary heteroalkyl moiety is a glycine residue, i.e., —HNCH$_2$C(O)—

In various embodiments, the G-CSF peptide conjugate described above is produced according to a method comprising (a) contacting a substrate G-CSF peptide with a polymer-sialic acid donor having the formula:

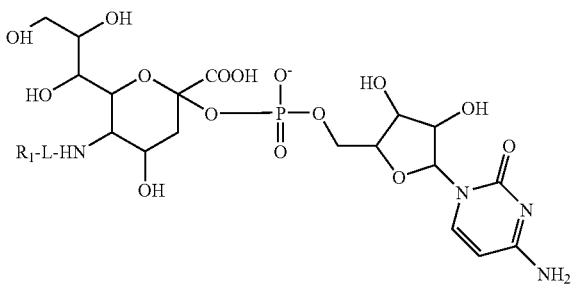

(II)

wherein $R_1$ and L are as defined above, and an enzyme that is capable of transferring the polymer-sialic acid moiety from the donor onto the glycosyl residue of the substrate G-CSF peptide. In an exemplary embodiment, the polymer is a poly (alkylene glycol), e.g., PEG. In one embodiment, the enzyme is a sialyltransferase, e.g., ST6GalNAcI, as described in WO 2005/055946.

The G-CSF peptide conjugate described above can be produced according to a method comprising: (a) contacting an unglycosylated substrate G-CSF peptide with a glycosyl donor and an enzyme that is capable of transferring the glycosyl moiety from the donor onto the substrate G-CSF peptide, and (b) contacting the glycosylated G-CSF peptide from (a) with a polymer-sialic acid donor having a structure according to Formula (II).

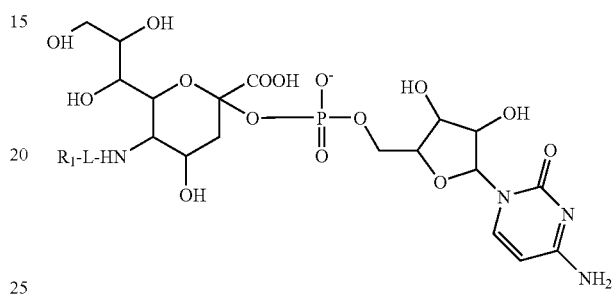

(II)

wherein $R_1$ and L are as defined above, and an enzyme that is capable of transferring the polymer-sialic acid moiety from the donor onto the glycosyl residue of the substrate G-CSF peptide. In an exemplary embodiment, the polymer is a poly (alkylene glycol), e.g., PEG. The steps (a) and (b) are either sequential or simultaneous reactions. In an exemplary embodiment, the glycosyl donor is UDP-N-acetylgalactosamine. In an exemplary embodiment, the enzyme in (a) is an N-acetylgalactosaminyltransferase and the enzyme in (b) is a sialyltransferase, e.g. GalNAcT2 in (a) and ST6GalNAcI.

The G-CSF peptide can be produced by chemical synthetic procedures or can be of any human or another mammalian source and can be obtained by purification from naturally occurring sources like human placenta, human blood or human urine. For example, a number of epithelial carcinomas, acute myeloid leukaemia cells and various tumor cell lines are capable of expressing this factor.

In various embodiments, the G-CSF is recombinantly produced. An exemplary procedure for recombinant production includes prokaryotic or eukaryotic host expression of an exogenous DNA sequence. In exemplary embodiments, the DNA sequence is obtained by genomic or cDNA cloning or by DNA synthesis. Representative prokaryotic hosts include bacteria, e.g., *E. coli*. A non-limiting example of useful eukaryotic hosts includes yeast. In various embodiments, the yeast is *S. cerevisiae*. In an exemplary embodiment the host is a mammalian cell, e.g., Chinese hamster ovary (CHO) cells and monkey cells.

Examples of recombinant production of a protein, e.g., G-CSF are known in the art. In general, this includes the transfection of host cells with an appropriate expression vector, the cultivation of the host cells under conditions which enable the production of the protein and the purification of the protein from the host cells. For detailed information see e.g. Souza, L. M. et al. 1986, Recombinant human granulocyte colony-stimulating factor: effects on normal and leukemic myeloid cells, *Science* (1986) 232: 61-65; Nagata, S. et al. 1986, Molecular cloning and expression of cDNA for human granulocyte colony-stimulating factor, *Nature* (1986) 319: 415-418; Komatsu, Y. et al. 1987, Cloning of granulocyte colony-stimulating factor cDNA from human macrophages and its expression in *Escherichia coli*, *Jpn. J. Cancer Res.* (1987) 78: 1179-1181.

In various embodiments, the G-CSF has the amino acid sequence of human mature G-CSF (see e.g., Nagata, S. et al. (1986), supra), and may further contain a methionine at its amino terminus, which then results in a protein of 175 amino acids (see SEQ ID NO:1 above). Furthermore, instead of the methionine, G-CSF may contain another non-methionine amino acid residue, e.g., serine or a threonine residue.

In an exemplary embodiment, the protein is purified according to a downstream processing protocol. Exemplary suitable purification methods for G-CSF are described in the art, e.g. in WO 87/01132, EP 0719860 A, EP 1 458757 A, EP 1 527 188 A, WO 03/051922, WO 01/04154 and WO 2006/097944.

In one embodiment of the present invention the polymer-G-CSF peptide conjugate is prepared as described in Example 1 provided herein. This conjugate is includes a G-CSF polypeptide and a PEG moiety linked via an N-acetyl-galactosaminyl (GalNAc) group, which is bound to a sialic acid (SA) residue. An exemplary conjugate has the structure G-CSF-GalNAc-SA-PEG as follows:

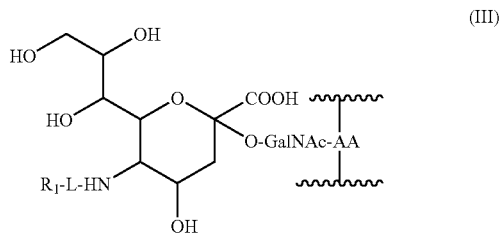

(III)

wherein $R_1$ and L are as defined above and AA is an amino acid residue of G-CSF. The PEG moiety is linear or branched. In various embodiments, AA is a threonine, e.g., Threonine 133 (Threonine 134 if an N-terminal methionine is present). In selected embodiments, L is heteroalkyl moiety, e.g., an amino acid residue, e.g., glycine (—HNCH$_2$C(O)—).

In an exemplary embodiment, $R_1$ is a linear PEG moiety linked via a sialic acid group and a GalNAc group to an amino acid residue of a G-CSF polypeptide as shown below:

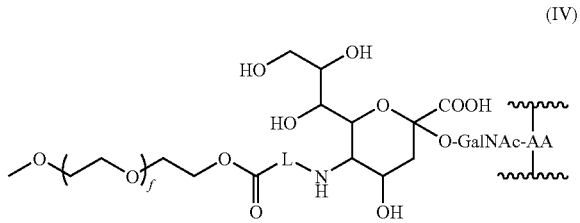

(IV)

wherein L is as defined above; AA is an amino acid residue of G-CSF. In an exemplary embodiment, f is selected from the integers 1 to 2500. In various embodiments, f is an integer selected such that the PEG moiety has a molecular weight of about 5 Kd, about 10 kD, about 15 KD or about 20 KD. In various embodiments, AA is a threonine, e.g., Threonine 133 (Threonine 134 if an N-terminal methionine is present). In selected embodiments, L is heteroalkyl moiety, e.g., an amino acid residue, e.g., glycine (—HNCH$_2$C(O)—).

In certain embodiments, the polymer G-CSF conjugate has the following formula:

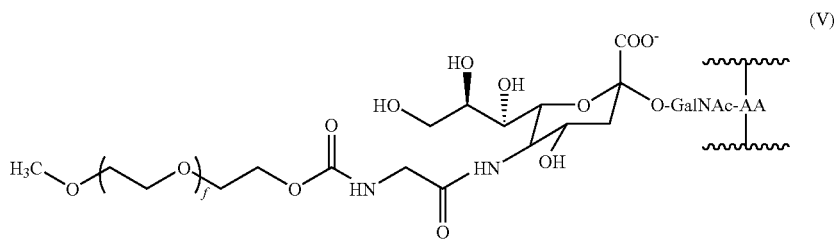

(V)

in which AA is an amino acid residue of G-CSF. In an exemplary embodiment, f is selected from the integers 1 to 2500. In various embodiments, f is an integer selected such that the PEG moiety has a molecular weight of about 5 Kd, about 10 kD, about 15 KD or about 20 KD. In various embodiments, AA is a threonine, e.g., Threonine 133 (Threonine 134 if an N-terminal methionine is present). In selected embodiments, L is heteroalkyl moiety, e.g., an amino acid residue, e.g., glycine (—HNCH$_2$C(O)—).

The pharmaceutical preparation of the present invention is a liquid composition, e.g. an aqueous solution. For injection purposes, the use of pure water as solvent is preferred. Other solvents which are suitable and conventional for pharmaceutical preparations can, however, also be employed. In a preferred embodiment of the invention, the pharmaceutical compositions are isotonic solutions.

Further, in an exemplary embodiment, there is no need for reconstitution at any stage of the preparation of the liquid solution formulation of the invention. The solution is a ready-to-use formulation.

Various pharmaceutical compositions of the invention have a pH in the range of about 4.5 to about 5.5. Further exemplary formulations have a pH value from about 4.7 to about 5.3, others have a pH value from about 4.8 to about 5.2 and still other formulations have a pH value from about 4.9 to about 5.1.

If an adjustment is required in order to achieve the desired pH range, the pH value is adjusted by means of suitable solutions; with acidic solutions if a reduction of the pH value is indicated and with alkaline solutions in case an increase of the pH value is indicated. Non-limiting examples of suitable acidic solutions are, e.g., hydrochloric acid, phosphoric acid, citric acid and sodium or potassium hydrogen phosphate. Non-limiting examples of suitable alkaline solutions are alkali and alkali earth hydroxides, alkali carbonates, alkali acetates, alkali citrates and dialkali hydrogen phosphates, e.g. sodium hydroxide, sodium acetate, sodium carbonate, sodium citrate, disodium or dipotassium hydrogen phosphate or ammonia.

In an exemplary embodiment, the pH of the solution is adjusted using sodium hydroxide. As a consequence, the formulation of the invention may contain sodium ions. In various embodiments, sodium is present in a concentration of less than 10 mmol/L, typically, less than 6 mmol/L.

In various embodiments, the pharmaceutical formulation of the invention comprises one or more surfactants. Non-limiting examples of useful surfactants include: nonionic surfactants, e.g., sorbitan fatty acid esters, e.g., sorbitan monocaprylate, sorbitan monolaurate, sorbitan monopalmitate; glycerin fatty acid esters, e.g., glycerin monocaprylate, glycerin monomyristate, glycerin monostearate; polyglycerin fatty acid esters, e.g., decaglyceryl monostearate, decaglyceryl distearate, decaglyceryl monolinoleate; polyoxyethylene sorbitan fatty acid esters, e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters, e.g., polyoxyethylene sorbitol tetrastearate, polyoxyethylene sorbitol tetraoleate; polyoxyethylene glycerin fatty acid esters, e.g., polyoxyethylene glyceryl monostearate; polyethylene glycol fatty acid esters, e.g., polyethylene glycol distearate; polyoxyethylene alkyl ethers, e.g., polyoxyethylene lauryl ether; polyoxyethylene polyoxypropylene alkyl ethers, e.g., polyoxyethylene polyoxypropylene glycol ether, polyoxyethylene polyoxypropylene propyl ether, polyoxyethylene polyoxypropylene cetyl ether; polyoxyethylene alkyl phenyl ethers, e.g., polyoxyethylene nonyl phenyl ether; polyoxyethylene hardened castor oils, e.g., polyoxyethylene castor oil, polyoxyethylene hardened castor oil (polyoxyethylene hydrogenated castor oil); polyoxyethylene beeswax derivatives, e.g., polyoxyethylene sorbitol beeswax; polyoxyethylene lanolin derivatives, e.g., polyoxyethylene lanolin; polyoxyethylene fatty acid amides, e.g., as polyoxyethylene stearic acid amide having an HLB of 6-18; anionic surfactants, e.g., alkyl sulfates having a $C_{10}$-$C_{18}$ alkyl group, e.g., sodium cetylsulfate, sodium laurylsulfate, sodium oleylsulfate; polyoxyethylene alkyl ether sulfates having an average EO mole number of 2-4 and a $C_{10}$-$C_{18}$ alkyl group, e.g., sodium polyoxyethylene laurylsulfate; alkyl sulfosuccinic acid ester salts having a $C_{8}$-$C_{18}$ alkyl group, e.g., sodium laurylsulfosuccinate; and natural surfactants, e.g., lecithin; glycerophospholipids; sphingophospholipids, e.g., sphingomyelin; sucrose fatty acid esters of $C_{12}$-$C_{18}$ fatty acids. One or more of these surfactants may be added in combination to formulations of the present invention.

Preferred surfactants are polyoxyethylene sorbitan alkyl esters, more preferably Polysorbates 20, 21, 40, 60, 65, 80, 81, 85, most preferably Polysorbates 20 and 80.

The concentration of the surfactant in the formulation is typically in the range of from about 0.0005% (w/v) to about 0.05% (w/v), preferably from about 0.001% (w/v) to about 0.01% (w/v), more preferably from about 0.002% (w/v) to about 0.006% (w/v) and more preferably from about 0.003% (w/v) to about 0.004% (w/v), based on the total volume of the solution formulation.

In an exemplary embodiment, the formulations of the invention contain the surfactant Polysorbate 20 or 80 in a concentration of about 0.003% (w/v), about 0.0033% (w/v) or about 0.004% (w/v). Polysorbate 20 is preferred.

The formulation according to the invention comprises a physiologically acceptable buffering agent. Suitable buffers are known in the art of solution formulations, e.g., phosphate buffers (preferably sodium monohydrogen phosphate—sodium dihydrogen phosphate system), citrate buffers, lactate buffers, acetate buffers, carbonate buffers, BisTris, MES, and glycine-HCl. In various embodiments, an acetate buffer, e.g., acetic acid or a salt thereof, is utilized. Exemplary buffer salts include alkali or ammonium salts.

In an exemplary embodiment, the buffering agent is present in the formulation in a concentration of from about 1 to about 100 mmol/L, preferably from about 2 to about 50 mmol/L and most preferably from about 5 to about 20 mmol/L. In a preferred embodiment the buffer is present at about 10 mmol/L, most preferably it is acetate present at about 10 mmol/L.

The concentration of the buffer, e.g., acetate, is chosen in such a way that the pH stabilizing action as well as sufficient buffering capacity is provided. It is preferable to simultaneously keep the ion concentration and hence the conductivity of the solution as low as possible in order to avoid the formation of aggregates.

In an embodiment of the invention the conductivity of the final solution formulation is less than about 1.0 mS/cm, preferably less than about 0.8 mS/cm and more preferably less than about 0.5 mS/cm.

Further, it is preferred that the preparation is free from tartaric acid and succinic acid and salts thereof. It is also preferred that the solution is free from HEPES, TES and tricine.

It is also preferred that the formulation of the invention is free from sulfate ions.

Further, in a preferred embodiment, the formulation is free from preservatives. As used herein, preservatives are substances, which are conventionally used as preservatives for increasing storage stability and which, in standard concentrations, have a bactericidal effect. In particular, the formulation does not contain preservatives like chloroethane, benzyl alcohol, p-chloro-m-cresol, and pyrocarbonic acid dialkyl ester, and benzalkonium chloride.

In an embodiment of the invention, the formulation further comprises a polyol, preferably a sugar alcohol, most preferably mannitol or sorbitol as a tonicity modifying agent. Sorbitol is especially preferred. The amount of sugar, e.g., sorbitol or mannitol is usually up to about 10.0% (w/v), based on the total volume of the solution. Preferably, the concentration is up to about 8.0% (w/v), more preferably up to about 6.0% (w/v) and most preferably about 5.0% (w/v). In a preferred embodiment, sorbitol is present in an amount of about 5.0% (w/v).

Further, it is preferred that the solution formulation of the invention does not contain a stabilising agent selected from amino acids, derivatives and salts thereof, polymeric stabilizing agents and proteinaceous stabilizing agents.

The polymer-G-CSF conjugate containing formulations of the present invention are normally administered via parenteral routes, e.g., injection (subcutaneous, intravenous or intramuscular injection) or percutaneous, mucosal, nasal or pulmonary administration, but may also be orally administered.

The polymer-G-CSF conjugate is usually present in the formulation in a concentration of from about 1.0 to about 30.0 mg/mL, preferably from about 5.0 to about 20.0 mg/mL and most preferably from about 8.0 to about 12.0 mg/mL. In a preferred embodiment, the polymer-G-CSF conjugate is PEG-SA-GalNAc-G-CSF (e.g., according to Formula I, III, IV or V above) and it is present in an amount of 10.0 mg/mL.

In a preferred embodiment the formulation comprises the polymer-G-CSF conjugate (e.g., according to Formula I, III, IV or V above) as active ingredient, a surfactant, a buffering agent, a tonicity modifying agent, sodium ions and water, and essentially no other constituent. Most preferably the aqueous preparation according to the invention contains a glycoPEGylated G-CSF as active agent, Polysorbate 20 and/or Polysorbate 80 as surfactant, sorbitol and/or mannitol as tonicity modifier, acetate as buffer and sodium, and essentially no other additives or excipients.

In another aspect of the invention the aqueous preparation of the invention as described above is diluted to obtain an aqueous dilution preparation that is suited for pediatric use. Appropriate dilutions for the treatment of children are obtained by diluting the above described solution of the invention about 1:2 to about 1:8.

The invention also relates to a pharmaceutical container containing the aqueous preparation of the invention or a dilution solution obtained therefrom by dilution. Suitable pharmaceutical containers are known in the art. The container may, for example, be a syringe, vial, infusion bottle, ampoule or carpoule. In a preferred embodiment, when the container is a syringe, the syringe is equipped with a needle protection system. Such needle protection systems which are well known from the prior art help to reduce the risk of injuries. In another embodiment, the container is a carpoule within an injection pen.

The present invention also relates to a method of preparing an aqueous preparation of the invention, wherein the polymer-G-CSF conjugate as the active agent is formulated in an aqueous preparation having a pH in the range of 4.5 to 5.5 and comprising a surfactant and further pharmaceutical excipients.

In various embodiments, the invention relates to the use of an aqueous preparation of the invention in the treatment or prevention of neutropenia. Further, the aqueous preparation of the invention can be advantageously used in the treatment or prevention of neurological disorders or in connection with bone marrow transplantation. In general, the pharmaceutical solutions of the invention are useful for stem cell mobilization.

The pharmaceutical liquid formulation according to the invention was found to exhibit a very good storage stability. Within the scope of the present invention, the term "storage stable" is understood to mean that the content of active polymer-G-CSF conjugate still amounts to 80% or more of the initial concentration of this agent after three months of storage of the formulation at 25° C. Preferably, after storage for three months at 25° C., the remaining content of G-CSF activity still amounts to at least 85%, more preferably at least 90%, and most preferably at least 95% of the original activity.

The activity of the polymer-G-CSF conjugate can be determined by means of conventional activity tests, as they are described in the prior art for G-CSF; see e.g. Draft Monographie "Filgrastim Concentrated Solution" Pharm Eur. Vol. 19, No. 1, January 2007, or Stute, N., et al. "Pharmacokinetics of subcutaneous recombinant human granulocyte colony-stimulating factor in children 1" (1992) *Blood* 79 (11), pages 2849-2854.

The measurement of G-CSF activity in vitro is described, e.g., by Shirafuji, N. et al. 1989, A new bioassay for human granulocyte colony-stimulating factor (hG-CSF) using murine myeloblastic NFS-60 cells as targets and estimation of its levels in sera from normal healthy persons and patients with infectious and hematological disorders, *Exp. Hematol.* (1989) 17, 116-119. For the measurement of G-CSF activity in vivo see e.g. Tanaka, H. et al. 1991, Pharmacokinetics of recombinant human granulocyte colony-stimulating factor conjugated to polyethylene glycol in rats, *Cancer Research* (1991) 51, 3710-3714. Further publications where tests for the measurement of the activity of G-CSF are described are U.S. Pat. No. 6,555,660; Nohynek, G. J. et al. 1997, Comparison of the potency of glycosylated and nonglycosylated recombinant human granulocyte colony-stimulating factors in neutropenic and normeutropenic CD rats, *Cancer Chemother. Pharmacol.* (1997) 39, 259-266.

In various embodiments, the purity of the polymer-G-CSF conjugate used in the formulation according to the invention is at least 95%, preferably at least 97%, more preferably at least 99% and most preferably more than 99%. The degree of purity can be determined by means of HPLC analysis. Suitable materials and protocols for conducting such analyses can be obtained from commercial suppliers, e.g., Vydac or TOSOH Bioscience (www.tosohbiosep.de).

The components for formulating the solutions according to the invention can be obtained from conventional sources, for example from companies, e.g., Sigma or Merck.

The production of the formulation of the invention can be performed according to conventional methods. The components of the formulation can be dissolved in an aqueous buffer. Alternatively, the conjugate can already be obtained in an aqueous buffer as the result of the purification process.

In certain embodiments of the invention, the finished liquid formulation is filled into a suitable pharmaceutical container, where it is stored until administration.

In summary, in various embodiments, the present invention provides an aqueous preparation comprising a polymer-G-CSF conjugate, wherein the preparation has a pH in the range of 4.5 to 5.5 and, optionally, further comprises a surfactant.

In various embodiments, the invention provides an aqueous preparation as described in the paragraph above, wherein the polymer is polyalkylene glycol.

In various embodiments, the invention provides an aqueous preparation according to either of the paragraph, wherein the polymer and G-CSF are linked via a glycosyl linker.

In exemplary embodiments, the invention provides an aqueous preparation according to any paragraph above, wherein the glycosyl linker is attached to an amino acid of the G-CSF peptide via O-glycosylation.

In various embodiments, the invention provides an aueous preparation according to any of the paragraphs above, wherein the glycosyl linker is attached to a threonine residue of the G-CSF protein, for example, Thr 134, based on the amino acid sequence of methionyl-G-CSF protein or Thr 133, based on the amino acid sequence of naturally occurring human G-CSF.

In an exemplary embodiment according to any of the paragraphs above, the invention provides an aqueous preparation, wherein the glycosyl linker comprises a mono-, di- or oligosaccharide.

In various embodiments, the invention provides an aqueous preparation according to any of the paragraphs above, wherein the glycosyl linker comprises sialic acid and N-acetylgalactosamine. In a selected embodiment, the GalNAc moiety is attached to an amino acid of the G-CSF peptide.

In an exemplary embodiment, the invention provides an aqueous preparation according to any of the preceding paragraphs, wherein the surfactant is present in a concentration of from about 0.0001% (w/v) to about 0.05% (w/v). Non-limiting examples of surfactants include polyoxy ethylene sorbitan alkyl esters, e.g., Polysorbate 20 or Polysorbate 80.

In representative embodiments, the invention provides an aqueous preparation according to any of the preceding paragraphs, wherein the pH is in the range of from about 4.7 to about 5.3, e.g., 4.9 to 5.1.

In various embodiments, according to any of the preceding paragraphs, the aqueous composition of the invention further comprises a physiologically acceptable buffering agent, e.g., a buffering agent comprising acetic acid and/or a salt thereof. An exemplary concentration for a buffering agent is from about 2 to about 50 mmol/L.

In an exemplary embodiment, the aqueous preparation according to any of the preceding paragraphs, further comprises a tonicity modifying agent, e.g., sorbitol, mannitol and a combination thereof. Exemplary concentrations for the tonicity modifying agent are from about 1 to about 10%.

In various embodiments according to any of the preceding paragraphs, the preparation is free or essentially from stabilizing agents. Exemplary stabilizing agents from which the preparation is free or essentially free include amino acids, polymeric stabilizing agents and proteinaceous stabilising agents.

In exemplary embodiments, according to any of the preceding paragraphs, the preparation is free or essentially free from preservatives. Exemplary preservatives from which the preparation is free or essentially free include sulfate ions.

In an exemplary preparation according to any of the preceding paragraphs, the preparation includes sodium ions. An exemplary source of sodium ions is the use pf NaOH to adjust the pH of the preparation.

An exemplary aqueous preparation of the invention according to any of the preceding paragraphs includes a polymer-G-CSF conjugate as active agent, Polysorbate 20 and/or Polysorbate 80 as surfactant, sorbitol and/or mannitol as tonicity modifier, acetate as buffer and sodium, and no other excipients.

In various embodiments according to any of the preceding claims, the polymer-G-CSF conjugate is present in a concentration of from about 1 to about 20 mg/mL, e.g., from about 8 to about 12 mg/mL.

The aqueous preparation can be diluted and an exemplary aqueous dilution preparation derived from the aqueous preparation according to any of the preceding paragraphs, wherein the aqueous preparation according to any of the preceding claims is diluted 1:2 to 1:8.

As will be apparent to those of skill, in an exemplary embodiment, the invention also provides a pharmaceutical container containing an aqueous preparation according to any of the preceding paragraphs. Exemplary pharmaceutical containers include a syringe, vial, infusion bottle, ampoule or carpoule, for example, a syringe equipped with a needle protection system or a carpoule within an injection pen.

In exemplary embodiments, the invention provides a process for preparing an aqueous preparation as set forth above, wherein the polymer-G-CSF conjugate is formulated in an aqueous preparation having a pH in the range of from about 4.5 to about 5.5 and comprises a surfactant and one or more pharmaceutically acceptable excipients.

The invention also provides for the use of an aqueous preparation as set forth above treatment or prevention of neutropenia. The method comprises administering a therapeutically effective dose of an aqueous preparation of the invention to a subject in need of treatment for neutropenia.

The invention also provides for the use of an aqueous preparation as set forth above treatment or prevention of neurological disorders. The method comprises administering a therapeutically effective dose of an aqueous preparation of the invention to a subject in need of treatment for a neurological disorder.

The invention also provides for the use of an aqueous preparation as set forth above in treatment related to bone marrow transplantation. The method comprises administering a therapeutically effective dose of an aqueous preparation of the invention to a subject in need of treatment in connection with bone marrow transplantation.

The invention also provides for the use of an aqueous preparation as set forth above for mobilizing stem cells. The method comprises administering an amount of an aqueous preparation of the invention sufficient to mobilize stem cells.

As will be appreciated by those of skill in the art, the invention also provides for the use of the recited methods of treatment for both pediatric and adult subjects.

The following Examples are intended to illustrate the invention without limiting its scope.

EXAMPLES

Example 1

Preparation of G-CSF-GalNAc-SA-PEG

The following example illustrates the preparation of G-CSF-GalNAc-SA-PEG in (a) a two sequential step method wherein each intermediate product is purified before it is used in the next step, and (b) a one step method using simultaneous addition of enzymes.

1a. The Two Step Method
Preparation of G-CSF-GalNAc (pH 6.2) from G-CSF and UDP-GalNAc using GalNAc-T2.

G-CSF (960 mcg) in 3.2 mL of packaged buffer was concentrated by utrafiltration using an UF filter (MWCO 5K) and then reconstituted with 1 mL of 25 mM MES buffer (pH 6.2, 0.005% $NaN_3$). UDP-GalNAc (6 mg, 9.24 mM), GalNAc-T2 (40 µL, 0.04 U), and 100 mM $MnCl_2$ (40 µL, 4 mM) were then added and the resulting solution was incubated at room temperature.

After 24 hrs, MALDI indicated the reaction was complete. The reaction mixture was directly subjected to HPLC purification using SEC (Superdex 75 and Superdex 200) and an elution buffer comprising of PBS (phosphate buffered saline, pH 4.9 and 0.005% Tween 80). The collected peak of G-CSF-GalNAc was concentrated using a Centricon 5 KDa MWCO filter to about 150 µL and the volume adjusted to 1 mL using PBS (phosphate buffered saline, pH 4.9 and 0.005% Tween 80). Final protein concentration 1 mg/mL ($A_{280}$), yield 100%. The sample was stored at 4° C.

Preparation of G-CSF-GalNAc-SA-PEG Using Purified G-CSF-GalNAc, CMP-SA-PEG (20 KDa) and Mouse ST6GalNAc-TI (pH 6.2).

The G-CSF-GalNAc solution containing 1 mg of protein was buffer exchanged into 25 mM MES buffer (pH 6.2, 0.005% $NaN_3$) and CMP-SA-PEG (20 KDa) (5 mg, 0.25 umol) was added. After dissolving, $MnCl_2$ (100 mcL, 100 mM solution) and ST6GalNAc-I (100 mcL, mouse enzyme) was added and the reaction mixture rocked slowly at 32° C. for three days. The reaction mixture was concentrated by ultrifiltration (MWCO 5K) and buffer exchanged with 25 mM NaOAc (pH 4.9) one time and then concentrated to 1 mL of total volume. The product was then purified using SP-sepharose (A: 25 mM NaOAc+0.005% tween-80 pH 4.5; B: 25 mM NaOAc+0.005% tween-80 pH 4.5+2M NaCl) at retention time 13-18 mins and SEC (Superdex 75; PBS-pH 7.2, 0.005% Tween 80) at retention time 8.6 mins (superdex 75, flow 1 mL/min) The desired fractions were collected, concentrated to 0.5 mL and stored at 4° C.

1b. One Step Method
One Pot Process using Mouse ST6GalNAc-I (pH 6.0).

G-CSF (960 µg of protein dissolved in 3.2 mL of the product formulation buffer) was concentrated by ultrafiltration (MWCO 5K) to 0.5 mL and reconstituted with 25 mM MES buffer (pH 6.0, 0.005% $NaN_3$) to a total volume of about 1 mL or a protein concentration of 1 mg/mL. UDP-GalNAc (6 mg, 9.21 µmol), GalNAc-T2 (80 µL, 80 mU), CMP-SA-PEG (20 KDa) (6 mg, 0.3 µmol) and mouse enzyme ST6GalNAc-I (120 µL) and 100 mM MnCl$_2$ (50 µL) were then added. The solution was rocked at 32° C. for 48 hrs and purified using standard chromatography conditions on SP-sepharose. A total of 0.5 mg of protein (A$_{280}$) was obtained or about a 50% overall yield. The product structure was confirmed by analysis with both MALDI and SDS-PAGE.

One Pot Process using Chicken ST6GalNAc-I (pH 6.0).

14.4 mg of G-CSF; was concentrated to 3 mL final volume, buffer exchanged with 25 mM MES buffer (pH 6.0, 0.05% NaN$_3$, 0.004% Tween 80) and the volume was adjusted to 13 mL. The UDP-GalNAc (90 mg, 150 µmole), GalNAc-T2 (0.59 U), CMP-SA-PEG-20 KDa (90 mg), chicken ST6GalNAc-I (0.44 U), and 100 mM MnCl$_2$ (600 mcL) were then added. The resulting mixture stood at room temperature for 60 hrs. The reaction mixture was then concentrated using a UF (MWCO 5K) and centrifugation. The residue (about 2 mL) was dissolved in 25 mM NaOAc buffer (pH 4.5) and concentrated again to 5 mL final volume. This sample was purified using SP-sepharose for about 10-23 min, SEC (Superdex 75, 17 min, flow rate 0.5 mL/min) and an additional SEC (Superdex 200, 23 min, flow rate 0.5 mL/min), to yield 3.6 mg (25% overall yield) of G-CSF-GalNAc-SA-PEG-20 KDa (A$_{280}$ and BCA method).

Example 2

Liquid Polymer-G-CSF Conjugate (PEG-SA-GalNAc-G-CSF) Formulation

A liquid formulation comprising glycoPEGylated G-CSF (the conjugate having the structure: PEG-SA-GalNAc-G-CSF) was prepared by formulating the following components in an aqueous acetate buffer solution.

| Ingredient | |
|---|---|
| glycoPEGylated G-CSF | 10 mg/mL |
| Acetate | 10 mM |
| Sorbitol | 5.0% (w/v) |
| Polysorbate 20 | 0.0033% (w/v) |
| Sodium | 4.38 mM |
| pH | 5.0 |

The pH value of the composition was adjusted by adding NaOH. All ingredients are of a quality according to the European Pharmacopoeia (Ph. Eur.).

In addition, the same composition was prepared having either pH 4.5 or pH 5.5 and proportionately less or more sodium, respectively. A comparative formulation was also prepared which has a pH of 4.0 (like that of the NEULASTA® (pegfilgrastim) preparation).

Example 3

Stability Tests of the Formulations According to the Present Invention

The compositions, pH 4.5, 5.0 and 5.5, were aliquoted in 500 µL/vials and stored at 2-8° C. and at 25° C.). After 1, 2, 3, 4.5, 6, 8, 12, and 15 months samples were tested for the test parameters given in the table below.

The expected specifications were as follows for the composition having a pH of 5.0:

| Test parameter | Method | Specification |
|---|---|---|
| Appearance | Visual inspection | Clear colorless |
| Content | UV-VIS | 10.0 mg/mL ± 5% |
| Content | RP-HPLC (30° C.) | 10.0 mg/mL ± 5% |
| Potency | Bioassay | 54-156% |
| Identity | SDS-PAGE | Conforms to reference standard |
| Purity | Western Blot | Conforms to reference standard |
| Purity | RP-HPLC (60° C.) | Oxidation < 2.0% |
| Purity | RP-HPLC (30° C.) | Non pegylated G-CSF 2.0% |
| Purity | SEC | Dimers and aggregates < 2.0% |

| Test parameter | Method | Specification |
|---|---|---|
| Deamidation | IEF | No additional bands detectable |
| pH | According to Ph. Eur. 5 and USP 28 | 5.0 ± 0.2 |
| Endotoxins | Test for bacterial endotoxins according to Ph. Eur. 5 | <5 EU/mg |
| Sterility | According to Ph. Eur. 5 | Sterile |
| Sub-visible particles | Particulate contamination: sub-visible particles according to Ph. Eur. 5 | <6000 particles ≧ 10 µm per vial; <600 particles ≧ 25 µm per vial |

All samples tested at T=0, 1 month, 2 months, 3 months, 4.5 months, 6 months, 8 months, 12 months and 15 months fulfilled the expected specifications. This was found for all tested compositions comprising glycoPEGylated G-CSF and having a pH of 4.5, 5.0 or 5.5.

The compositions of the invention were compared with two comparative formulations: NEULASTA® (pegfilgrastim) (pH 4.0) and a composition of glycoPEGylated G-CSF (PEG-SA-GalNAc-G-CSF) having a pH of 4.0. The results show that in comparison with the comparative solution comprising glycoPEGylated G-CSF and having a pH of 4.0, the formulations having higher pH values of 4.5, 5.0 and 5.5 show better storage stability. The collected data allow the conclusion that the higher pH values prevent acid hydrolysis of the glycoPEG bond. Further, it was observed that the formulations of the present invention have a stability that is comparable to the stability of the PEG-G-CSF conjugate known as NEULASTA® (pegfilgrastim).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An aqueous preparation comprising a polymer-G-CSF conjugate, wherein the preparation has a pH in the range of 4.5 to 5.5 and further comprises a surfactant and a buffering agent comprising acetic acid or a salt thereof, wherein the polymer-G-CSF conjugate comprises a polymer linked to G-CSF via a glycosyl linker.

2. The aqueous preparation according to claim 1, wherein the polymer is polyalkylene glycol.

3. The aqueous preparation according to claim 1, wherein the glycosyl linkage is via O-glycosylation.

4. The aqueous preparation according to claim 3, wherein the O-glycosylation is at a threonine residue of the G-CSF protein.

5. The aqueous preparation according to claim 4, wherein the threonine residue is Thr 134 based on the amino acid sequence of human methionyl-G-CSF protein or Thr 133 based on the amino acid sequence of naturally occurring human G-CSF.

6. The aqueous preparation according to claim 1, wherein the glycosyl linker comprises a mono-, di- or oligosaccharide.

7. The aqueous preparation according to claim 1, wherein the glycosyl linker comprises sialic acid and N-acetylgalactosamine.

8. The aqueous preparation according to claim 1, wherein the surfactant is present in a concentration of from about 0.0001% (w/v) to about 0.05% (w/v).

9. The aqueous preparation according to claim 1, wherein the surfactant is a polyoxy ethylene sorbitan alkyl ester.

10. The aqueous preparation according to claim 9, wherein the polyoxy ethylene sorbitan alkyl ester is Polysorbate 20 or Polysorbate 80.

11. The aqueous preparation according to claim 1, wherein the pH is in the range of about 4.7 to about 5.3.

12. The aqueous preparation according to claim 11, wherein the pH is in the range of from about 4.9 to about 5.1.

13. The aqueous preparation according to claim 1, wherein the buffering agent is present in a concentration of from about 2 to about 50 mmol/L.

14. The aqueous preparation according to claim 1, further comprising a tonicity modifying agent selected from sorbitol, mannitol and a combination thereof.

15. The aqueous preparation according to claim 14, wherein the tonicity modifying agent is present in a concentration of from about 1% to about 10% (w/v).

16. The aqueous preparation according to claim 1, wherein the preparation is free from stabilizing agents selected from amino acids, polymeric stabilizing agents, proteinaceous stabilizing agents and a combination thereof.

17. The aqueous preparation according to claim 1, wherein the preparation is free from preservatives.

18. The aqueous preparation according to claim 17, wherein the preparation is free from sulfate ions.

19. The aqueous preparation according to claim 1, wherein the pH is adjusted using NaOH.

20. The aqueous preparation according to claim 1, wherein the preparation contains sodium ions.

21. The aqueous preparation according to claim 1, wherein the preparation contains a polymer-G-CSF conjugate as active agent, Polysorbate 20 and/or Polysorbate 80 as surfactant, sorbitol and/or mannitol as tonicity modifier, acetate as buffer and sodium, and no other excipients.

22. The aqueous preparation according to claim 1, wherein the polymer-G-CSF conjugate is present in a concentration of from about 1 to about 20 mg/mL.

23. The aqueous preparation according to claim 22, wherein the polymer-G-CSF conjugate is present in a concentration of about 8 to about 12 mg/mL.

24. An aqueous dilution preparation obtained by diluting the aqueous preparation according to claim 1 from about 1:2 to about 1:8.

25. A pharmaceutical container containing an aqueous preparation according to claim 1.

26. The pharmaceutical container according to claim 25, wherein the container is a member selected from a syringe, vial, infusion bottle, ampoule and a carpoule.

27. The pharmaceutical container according to claim 26, wherein the container is a syringe equipped with a needle protection system.

28. The pharmaceutical container according to claim 25, wherein the container is a carpoule within an injection pen.

29. The aqueous preparation according to claim 1, wherein the aqueous preparation is free or essentially free of a stabilizing agent.

30. The aqueous preparation according to claim 1, further comprising a tonicity modifying agent, sodium ions, water, and essentially no other constituent.

31. A process for preparing an aqueous preparation according to claim 1, wherein the polymer-G-CSF conjugate as the active agent is formulated in an aqueous preparation having a pH in the range of 4.5 to 5.5, comprising a surfactant and one or more further pharmaceutical excipients.

32. A method of treating neutropenia, comprising administering to a subject in need of said treatment a therapeutically effective dose of an aqueous preparation according to claim 1, thereby treating the neutropenia.

33. A method of treating a neurological disorder, comprising administering to a subject in need of said treatment a therapeutically effective dose of an aqueous preparation according to claim 1, thereby treating the neurological disorder.

34. A method of treating a bone marrow transplant subject comprising administering a therapeutically effective dose of an aqueous preparation according to claim 1 to a subject who will or who has received a bone marrow transplant, thereby treating conditions associated with the bone marrow transplant in the subject.

35. A method of mobilizing stem cells, comprising administering to said cells a dose of an aqueous preparation according to claim 1 effective to mobilize the cells, thereby mobilizing the cells.

36. A method according to any of claim 32, 33 or 34, wherein said subject is a pediatric subject.

37. The method according to claim 33, wherein the neurological disorder is cerebral ischemia.

* * * * *

UNITED STATES PATENT AND TRADEMARK OFFICE
CERTIFICATE OF CORRECTION

PATENT NO. : 8,207,112 B2
APPLICATION NO. : 12/201705
DATED : June 26, 2012
INVENTOR(S) : Hinderer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 116 days.

Signed and Sealed this
Seventeenth Day of March, 2020

Andrei Iancu
*Director of the United States Patent and Trademark Office*

SEQUENCE LISTING

<160> NUMBER OF SEQ ID NOS: 2

<210> SEQ ID NO 1

```
<211> LENGTH: 175
<212> TYPE: PRT
<213> ORGANISM: Artificial Sequence
<220> FEATURE:
<223> OTHER INFORMATION: human methionyl-GCSF aa sequence as produced in
      E-coli

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 2
<211> LENGTH: 174
<212> TYPE: PRT
<213> ORGANISM: Artificial Sequence
<220> FEATURE:
<223> OTHER INFORMATION: GCSF aa sequence as produced in mammalian cells

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
130                 135                 140

Gln Arg Arg Ala Gly Gly Val Leu Val Ala Ser His Leu Gln Ser Phe
```

```
              145                 150                 155                 160
Leu Glu Val Ser Tyr Arg Val Leu Arg His Leu Ala Gln Pro
                    165                 170
```